(12) United States Patent
Foley et al.

(10) Patent No.: US 10,716,700 B2
(45) Date of Patent: Jul. 21, 2020

(54) NASAL INSERT AND CANNULA AND METHODS FOR THE USE THEREOF

(71) Applicant: TRUDELL MEDICAL INTERNATIONAL, London (CA)

(72) Inventors: Martin P. Foley, London (CA); Jerry Grychowski, Lake Zurich, IL (US)

(73) Assignee: Trudell Medical International, London (CA)

( * ) Notice: Subject to any disclaimer, the term of this patent is extended or adjusted under 35 U.S.C. 154(b) by 373 days.

(21) Appl. No.: 15/655,387

(22) Filed: Jul. 20, 2017

(65) Prior Publication Data
US 2018/0008453 A1    Jan. 11, 2018

Related U.S. Application Data

(63) Continuation of application No. 13/629,921, filed on Sep. 28, 2012, now Pat. No. 9,730,830.
(Continued)

(51) Int. Cl.
*A61F 5/56*    (2006.01)
*A61F 5/08*    (2006.01)

(52) U.S. Cl.
CPC .    *A61F 5/56* (2013.01); *A61F 5/08* (2013.01)

(58) Field of Classification Search
CPC ...... A61F 2/00; A61F 2/02; A61F 2/18; A61F 2/186; A61F 5/00; A61F 5/01; A61F 5/08;
(Continued)

(56) References Cited

U.S. PATENT DOCUMENTS

| 628,111 A | 7/1899 | McHatton |
|---|---|---|
| 669,098 A | 3/1901 | Overshiner |

(Continued)

FOREIGN PATENT DOCUMENTS

| EP | 1 157 663 A1 | 11/2001 |
|---|---|---|
| EP | 1 917 993 A1 | 5/2008 |

(Continued)

OTHER PUBLICATIONS

Extended European Search Report in European Application No. 07719844.8, dated Oct. 7, 2009, 7 pages.
(Continued)

*Primary Examiner* — Tarla R Patel
(74) *Attorney, Agent, or Firm* — Brinks Gilson & Lione

(57) ABSTRACT

A nasal insert includes a housing having a circumferential wall defining an interior passage. The wall has a longitudinal gap extending along a length thereof, with an outer peripheral dimension of the housing being adjustable by varying the gap. A valve is in communication with the interior passage and limits a fluid flow through the interior passage in at least one direction. In another embodiment, a nasal insert includes a user interface having a tubular housing defining an interior cavity open at opposite ends. An exterior surface of the housing is adapted to interface with a nasal vestibule of a user. A base is received in the interior cavity of the housing and includes an exit port. A cap is connected to the base and has an input port. A valve member is disposed in an interior passage defined by at least one of the cap and base, with the valve member being moveably received in the interior passage. Methods of using and assembling the nasal inserts also are provided.

17 Claims, 14 Drawing Sheets

Related U.S. Application Data

(60) Provisional application No. 61/540,740, filed on Sep. 29, 2011.

(58) Field of Classification Search
CPC ......... A61F 5/56; A61M 15/00; A61M 16/00; A61M 16/06; A61M 16/0666; A61M 16/0672; A61M 16/20; A61M 16/201; A61M 29/00; A61M 29/02; A61M 2029/025
USPC .............. 128/848, 857–858, 200.24, 200.26, 128/201.18, 201.23, 201.28, 203.22, 128/205.24, 206.18, 207.18; 606/191, 606/199, 204.45
See application file for complete search history.

(56) References Cited

U.S. PATENT DOCUMENTS

| | | |
|---|---|---|
| 675,275 A | 5/1901 | Gunning |
| 746,869 A | 12/1903 | Moulton |
| 774,446 A | 11/1904 | Moulton |
| 810,617 A | 1/1906 | Carence |
| 1,819,884 A | 8/1931 | Fores |
| 1,867,478 A | 7/1932 | Stelzner |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,370,305 A | 2/1968 | Goott et al. |
| 3,424,152 A | 1/1969 | Kuhlman |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,120,299 A | 10/1978 | Russo |
| 4,143,872 A | 3/1979 | Havstad et al. |
| 4,226,233 A | 10/1980 | Kritzer |
| 4,240,420 A | 12/1980 | Riaboy |
| 4,249,527 A | 2/1981 | Ko et al. |
| 4,267,831 A | 5/1981 | Aguilar |
| 4,325,366 A | 4/1982 | Tabor |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,601,465 A | 7/1986 | Roy |
| 4,739,987 A | 4/1988 | Nicholson |
| 4,822,354 A | 4/1989 | Elosegui |
| 4,854,574 A | 8/1989 | Larson et al. |
| 4,862,903 A | 9/1989 | Campbell |
| 4,878,513 A | 11/1989 | Ashby et al. |
| 4,908,028 A | 3/1990 | Colon et al. |
| 4,944,310 A | 7/1990 | Sullivan |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,415,660 A | 5/1995 | Campbell et al. |
| 5,425,359 A | 6/1995 | Liou |
| 5,459,544 A | 10/1995 | Emura |
| RE35,339 E | 10/1996 | Rapoport |
| 5,562,641 A | 10/1996 | Flomenblit et al. |
| 5,568,808 A | 10/1996 | Rimkus |
| 5,607,469 A | 3/1997 | Frey |
| 5,649,533 A | 7/1997 | Oren |
| 5,665,104 A | 9/1997 | Lee |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,816,241 A | 10/1998 | Cook |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,929,286 A | 7/1999 | Krumpelt et al. |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,083,141 A | 7/2000 | Hougen |
| 6,110,861 A | 8/2000 | Krumpelt et al. |
| D430,667 S | 9/2000 | Rome |
| 6,119,690 A | 9/2000 | Pantaleo |
| 6,177,482 B1 | 1/2001 | Cinelli et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,369,126 B1 | 4/2002 | Cinelli et al. |
| 6,386,197 B1 | 5/2002 | Miller |
| 6,443,944 B1 | 9/2002 | Doshi et al. |
| 6,484,725 B1 | 11/2002 | Chi |
| 6,558,831 B1 | 5/2003 | Doshi et al. |
| 6,561,188 B1 | 5/2003 | Ellis |
| 6,562,057 B2 | 5/2003 | Santin |
| 6,564,800 B1 | 5/2003 | Olivares |
| 6,568,387 B2 | 5/2003 | Davenport et al. |
| 6,585,639 B1 | 7/2003 | Kotmel et al. |
| 6,592,594 B2 | 7/2003 | Rimbaugh et al. |
| 6,595,215 B2 | 7/2003 | Wood |
| 6,626,172 B1 | 9/2003 | Karow et al. |
| 6,626,179 B1 | 9/2003 | Pedley |
| 6,632,554 B2 | 10/2003 | Doshi et al. |
| 6,679,264 B1 | 1/2004 | Deem et al. |
| 6,722,360 B2 | 4/2004 | Doshi |
| 6,756,144 B2 | 6/2004 | Issacci et al. |
| 6,863,066 B2 | 3/2005 | Ogle |
| 6,872,439 B2 | 3/2005 | Fearing et al. |
| 6,921,574 B2 | 7/2005 | Cinelli et al. |
| 6,997,177 B2 | 2/2006 | Wood |
| 7,001,684 B2 | 2/2006 | Doshi et al. |
| 7,011,723 B2 | 3/2006 | Full et al. |

(56) References Cited

U.S. PATENT DOCUMENTS

| | | |
|---|---|---|
| 7,047,969 B2 | 5/2006 | Noble |
| 7,156,098 B2 | 1/2007 | Dolezal et al. |
| 7,156,099 B1 | 1/2007 | Jenkins |
| 7,175,723 B2 | 2/2007 | Jones et al. |
| 7,178,524 B2 | 2/2007 | Noble |
| 7,201,169 B2 | 4/2007 | Wilkie et al. |
| D542,407 S | 5/2007 | Stallard et al. |
| 7,211,342 B2 | 5/2007 | Issacci et al. |
| 7,263,996 B2 | 9/2007 | Yung Ho |
| 7,334,581 B2 | 2/2008 | Doshi |
| 7,493,902 B2 | 2/2009 | White et al. |
| 7,506,649 B2 | 3/2009 | Doshi et al. |
| 7,615,304 B2 | 11/2009 | Ferrall et al. |
| 7,658,189 B2 | 2/2010 | Davidson et al. |
| 7,676,276 B2 | 3/2010 | Karell |
| 7,678,132 B2 | 3/2010 | Abbott et al. |
| 7,708,017 B2 | 5/2010 | Davidson et al. |
| 7,735,491 B2 | 6/2010 | Doshi et al. |
| 7,735,492 B2 | 6/2010 | Doshi et al. |
| 7,775,210 B2 | 8/2010 | Schobel et al. |
| 7,798,148 B2 | 9/2010 | Doshi et al. |
| 7,806,120 B2 | 10/2010 | Loomas et al. |
| 7,856,979 B2 | 12/2010 | Doshi et al. |
| 7,987,852 B2 | 8/2011 | Doshi et al. |
| 8,281,557 B2 | 10/2012 | Doshi et al. |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0062120 A1 | 5/2002 | Perkins et al. |
| 2002/0177031 A1 | 11/2002 | Doshi et al. |
| 2002/0177871 A1 | 11/2002 | Santin |
| 2003/0004498 A1 | 1/2003 | Doshi et al. |
| 2003/0054215 A1 | 3/2003 | Doshi et al. |
| 2003/0106555 A1 | 6/2003 | Tovey |
| 2003/0124401 A1 | 7/2003 | Issacci et al. |
| 2003/0140925 A1 | 7/2003 | Sapienza et al. |
| 2003/0154988 A1 | 8/2003 | Devore et al. |
| 2003/0158515 A1 | 8/2003 | Gonzalez et al. |
| 2003/0195552 A1 | 10/2003 | Santin |
| 2003/0209247 A1 | 11/2003 | O'Rourke |
| 2004/0016432 A1 | 1/2004 | Genger et al. |
| 2004/0020493 A1 | 2/2004 | Wood |
| 2004/0059368 A1 | 3/2004 | Maryanka |
| 2004/0067235 A1 | 4/2004 | Doshi |
| 2004/0141875 A1 | 7/2004 | Doshi |
| 2004/0146773 A1 | 7/2004 | Doshi et al. |
| 2004/0194779 A1 | 10/2004 | Doshi |
| 2004/0194780 A1 | 10/2004 | Doshi |
| 2004/0209134 A1 | 10/2004 | Issacci et al. |
| 2004/0261791 A1 | 12/2004 | Horian |
| 2005/0003262 A1 | 1/2005 | Doshi |
| 2005/0011524 A1 | 1/2005 | Thomlinson et al. |
| 2005/0051770 A1 | 3/2005 | Ando et al. |
| 2005/0133026 A1 | 6/2005 | Seleznev et al. |
| 2005/0284479 A1 | 12/2005 | Schrader et al. |
| 2006/0032497 A1 | 2/2006 | Doshi |
| 2006/0085027 A1 | 4/2006 | Santin et al. |
| 2006/0096596 A1 | 5/2006 | Occhialini et al. |
| 2006/0144398 A1 | 7/2006 | Doshi et al. |
| 2006/0150978 A1 | 7/2006 | Doshi et al. |
| 2006/0150979 A1 | 7/2006 | Doshi et al. |
| 2006/0283461 A1 | 12/2006 | Lubke et al. |
| 2007/0095349 A1 | 5/2007 | Hansmann et al. |
| 2007/0175478 A1 | 8/2007 | Brunst |
| 2007/0227542 A1 | 10/2007 | Kashmakov et al. |
| 2007/0277832 A1* | 12/2007 | Doshi ............... A61M 15/08 128/207.18 |
| 2007/0283962 A1 | 12/2007 | Doshi et al. |
| 2007/0295338 A1 | 12/2007 | Loomas et al. |
| 2008/0173309 A1 | 7/2008 | Doshi |
| 2008/0178874 A1 | 7/2008 | Doshi et al. |
| 2008/0221470 A1 | 9/2008 | Sather et al. |
| 2008/0275424 A1 | 11/2008 | Doshi et al. |
| 2009/0011323 A1 | 1/2009 | Guan et al. |
| 2009/0145441 A1 | 6/2009 | Doshi et al. |
| 2009/0145788 A1 | 6/2009 | Doshi et al. |
| 2009/0194100 A1* | 8/2009 | Minagi ............... A61F 5/08 128/200.24 |
| 2009/0194109 A1 | 8/2009 | Doshi et al. |
| 2009/0308398 A1 | 12/2009 | Ferdinand et al. |
| 2009/0308402 A1 | 12/2009 | Robitaille |
| 2009/0320851 A1 | 12/2009 | Selvarajan et al. |
| 2010/0031965 A1* | 2/2010 | Soderberg ............... A61F 5/56 128/848 |
| 2010/0147308 A1 | 6/2010 | Doshi et al. |
| 2010/0234789 A1 | 9/2010 | Batiste et al. |
| 2010/0234880 A1 | 9/2010 | Abbott et al. |
| 2010/0331777 A1 | 12/2010 | Danielsson |
| 2011/0005520 A1 | 1/2011 | Doshi et al. |
| 2011/0005528 A1 | 1/2011 | Doshi et al. |
| 2011/0005529 A1 | 1/2011 | Doshi et al. |
| 2011/0005530 A1 | 1/2011 | Doshi et al. |
| 2011/0218451 A1 | 9/2011 | Lai et al. |
| 2012/0111340 A1 | 5/2012 | Robitaille |
| 2013/0081637 A1 | 4/2013 | Foley et al. |

FOREIGN PATENT DOCUMENTS

| | | |
|---|---|---|
| FR | 2 210 109 A | 7/1974 |
| FR | 2 610 830 A | 8/1988 |
| GB | 2 126 101 A | 3/1984 |
| GB | 2 176 406 A | 12/1986 |
| GB | 2 324 729 A | 11/1998 |
| WO | WO 87/05798 A1 | 10/1987 |
| WO | WO 90/12614 A1 | 11/1990 |
| WO | WO 95/17220 A1 | 6/1995 |
| WO | WO 95/33520 A1 | 12/1995 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 02/38038 A2 | 5/2002 |
| WO | WO 2004/060438 A2 | 7/2004 |
| WO | WO 2004/060438 A3 | 7/2004 |
| WO | WO 2004/069110 A1 | 8/2004 |
| WO | WO 2006/063339 A2 | 6/2006 |
| WO | WO 2006/063339 A3 | 6/2006 |
| WO | WO 2007/023607 A1 | 3/2007 |
| WO | WO 2007/129814 A1 | 11/2007 |
| WO | WO 2007/134458 A1 | 11/2007 |

OTHER PUBLICATIONS

Extended European Search Report for European Application No. 12152742.8, dated Jul. 18, 2012, 11 pages.

European Search Report for Application No. 12835151.7 dated Jan. 14, 2016 6 pages.

International Search Report in International Application No. PCT/CA2007/000922, dated Aug. 14, 2007, 2 pages.

International Preliminary Report on Patentability for International Application No. PCT/CA2007/000922, dated Nov. 27, 2008, 5 pages.

International Search Report and Written Opinion of the International Searching Authority for International Application No. PCT/IB2012/001929, dated Jan. 16, 2013, 10 pages.

* cited by examiner

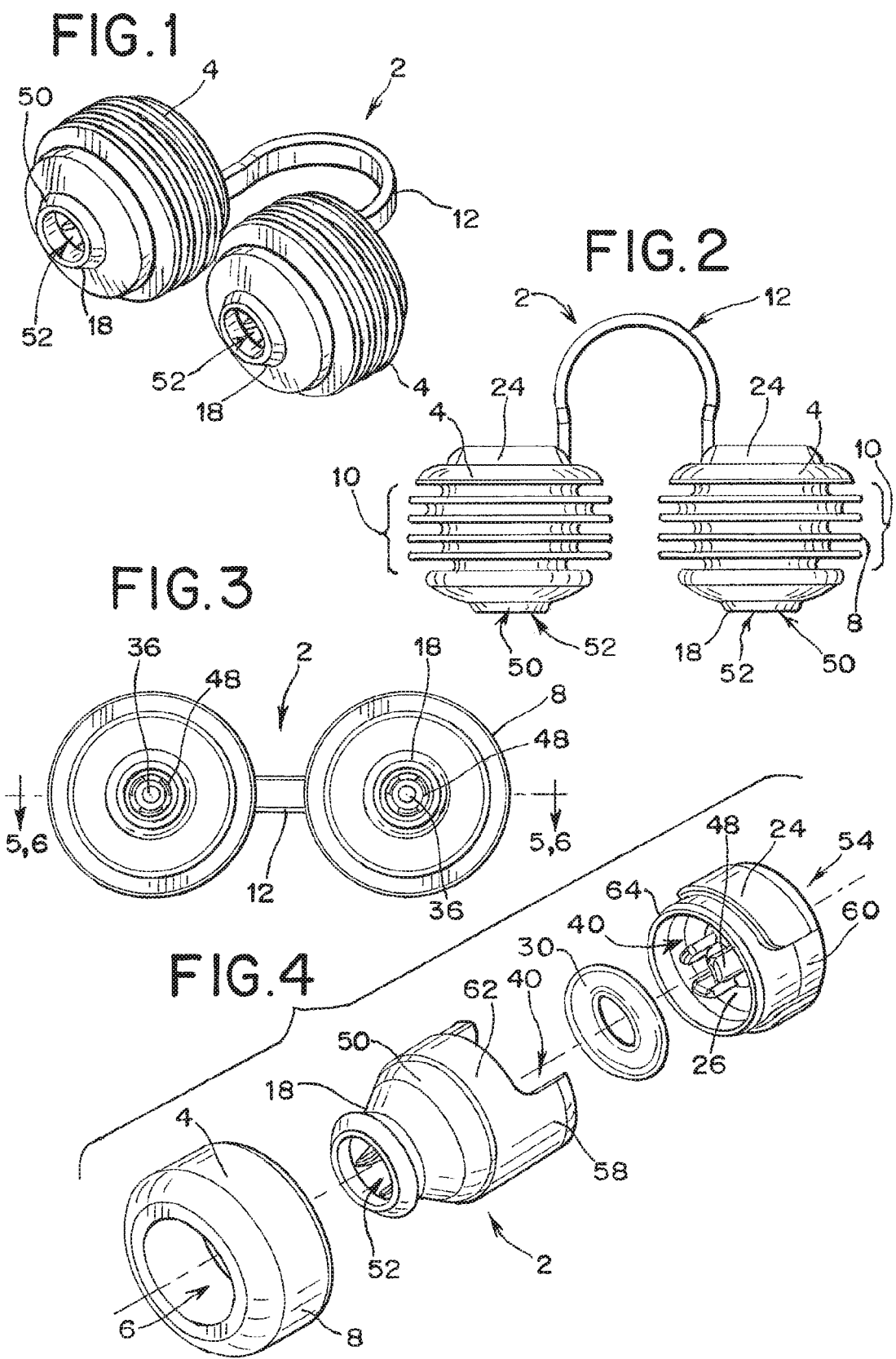

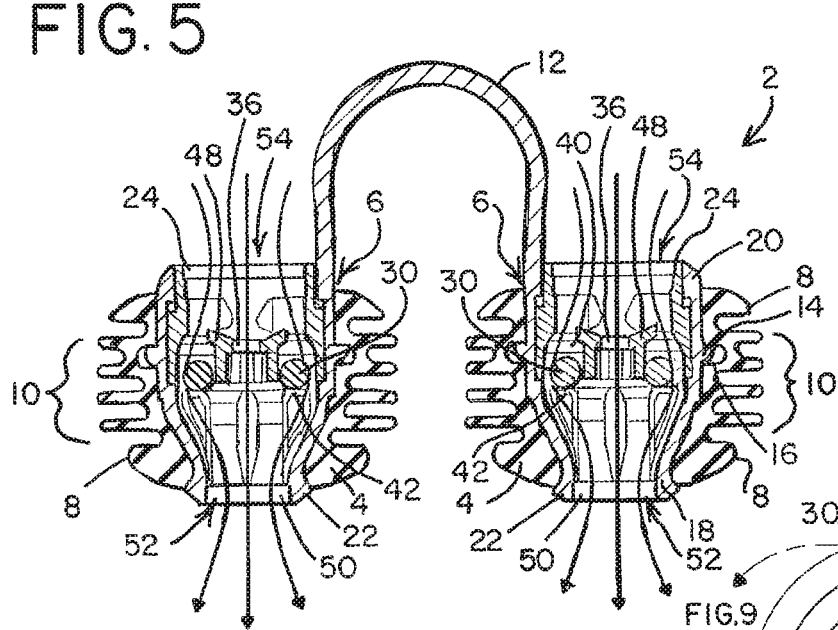
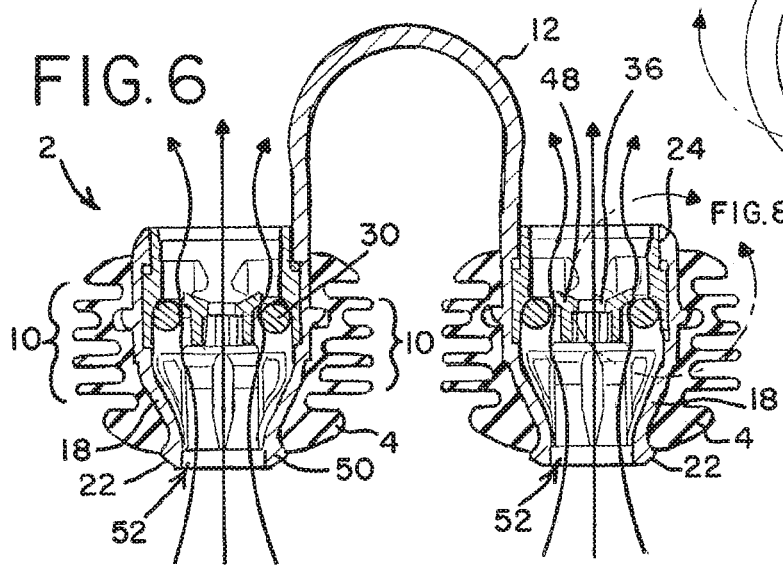
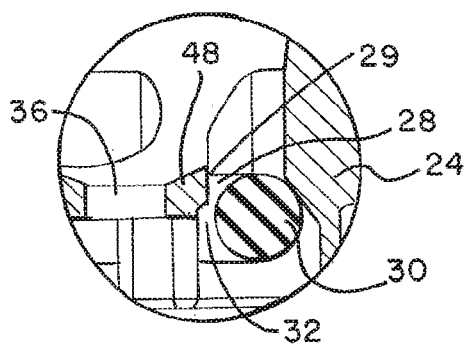
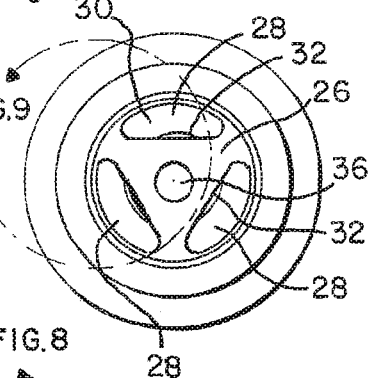
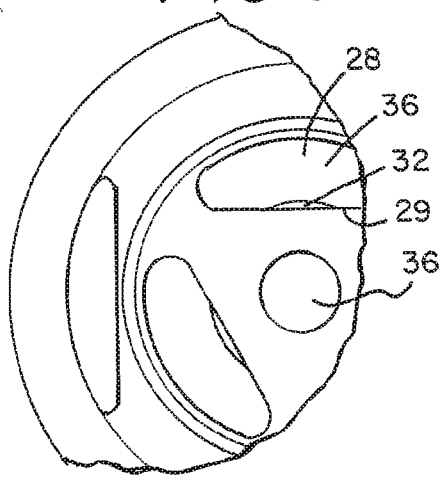

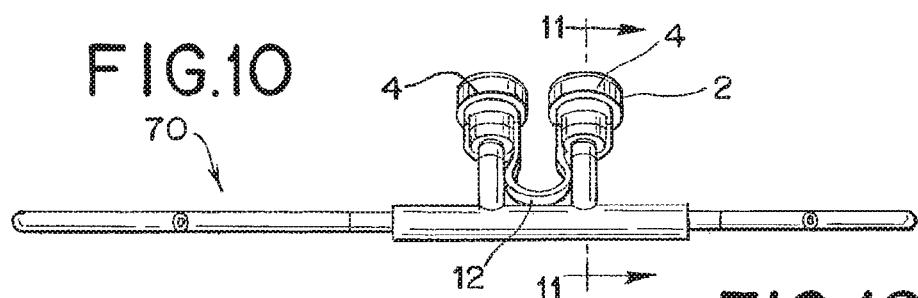
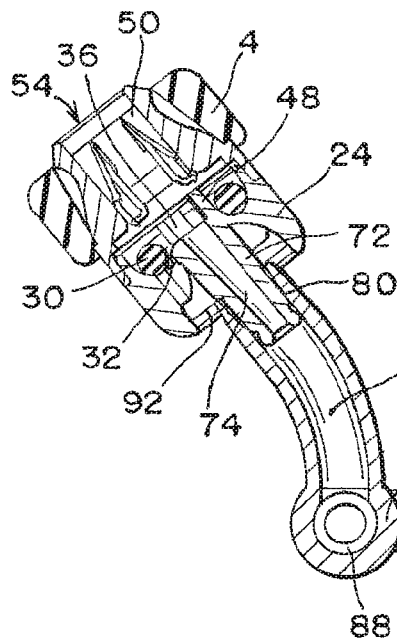
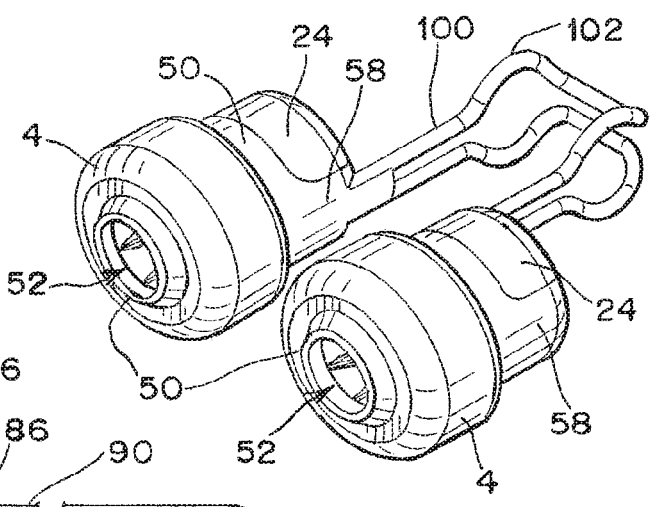
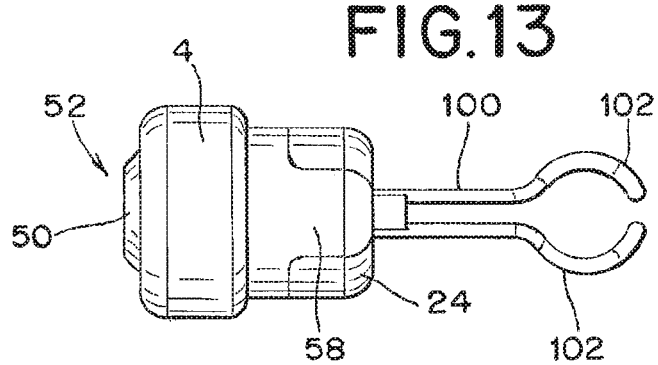
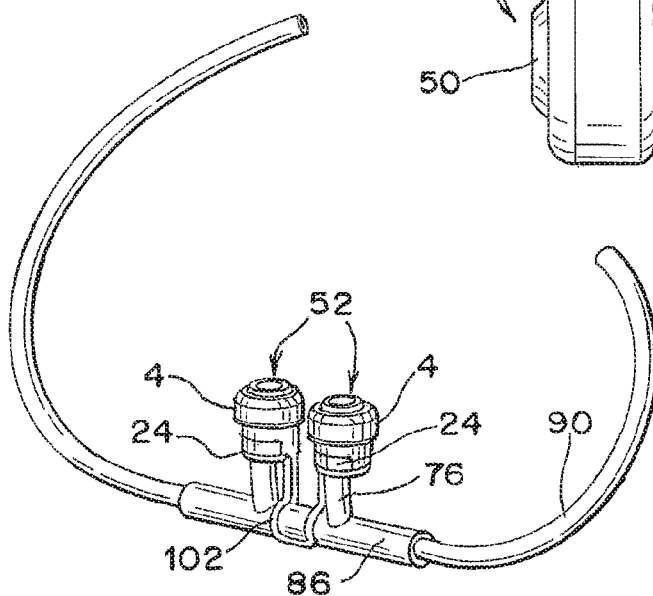

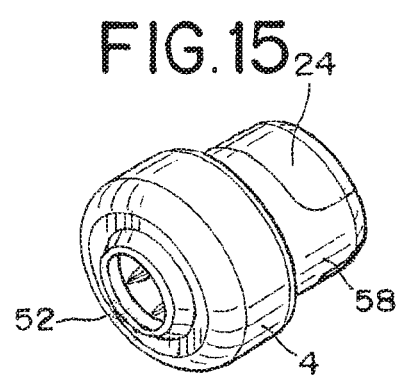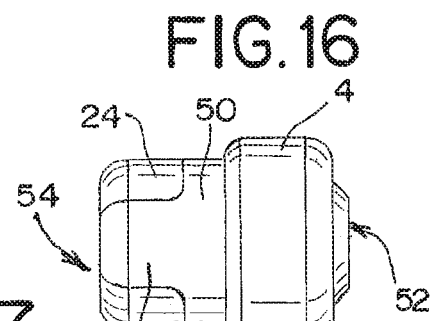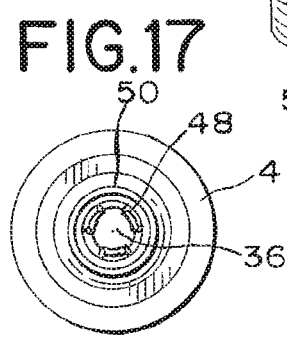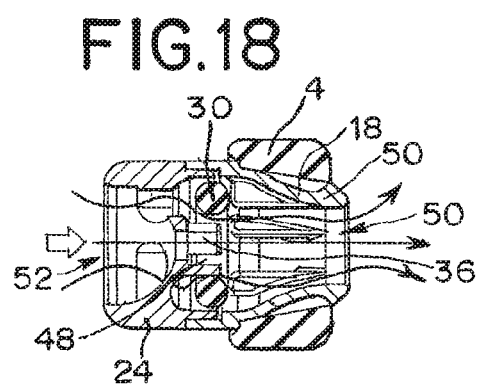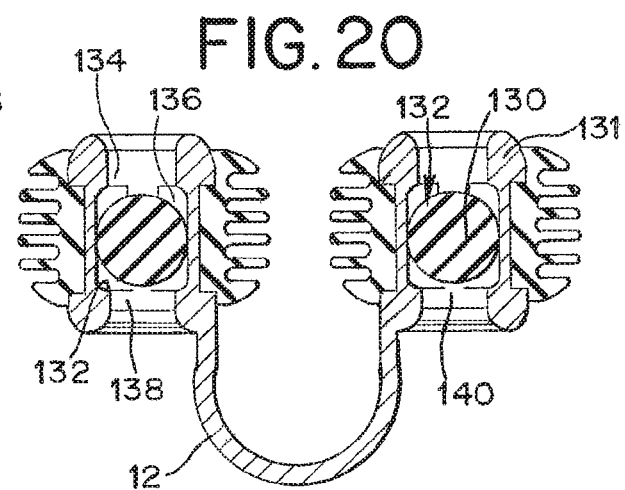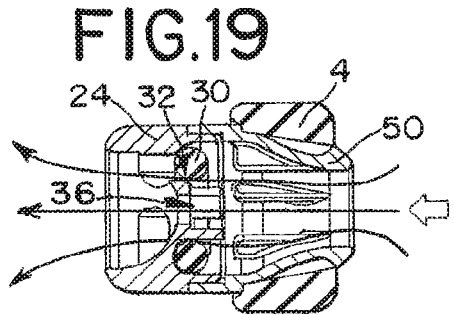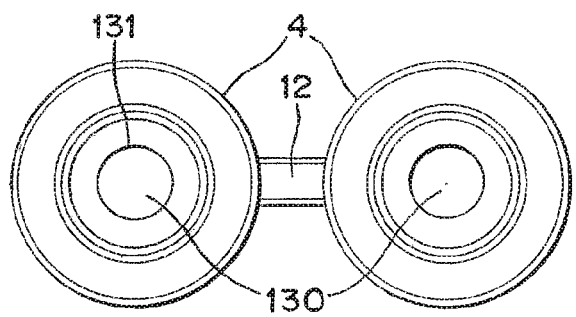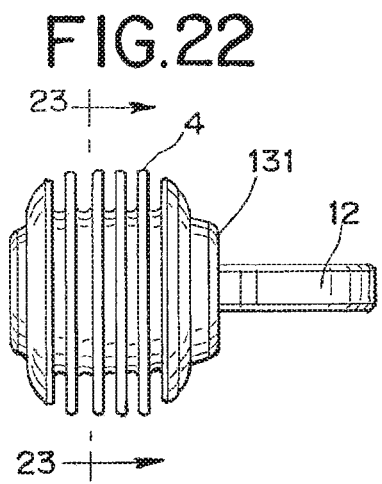

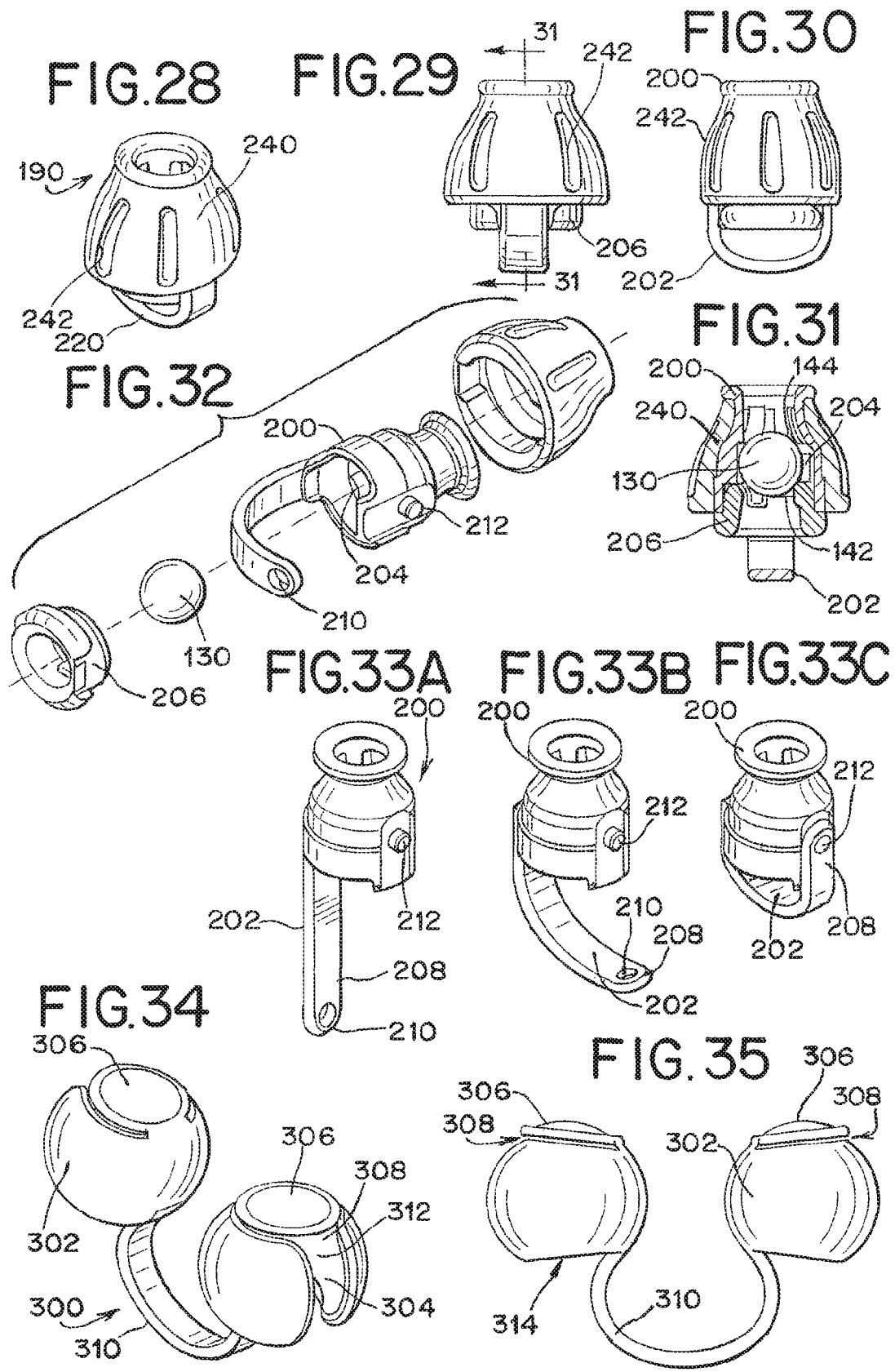

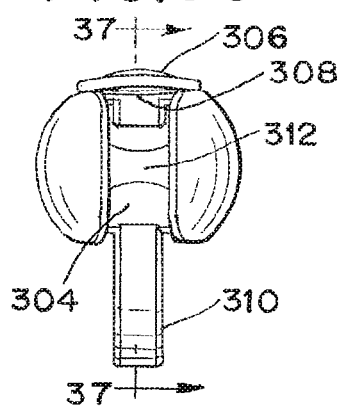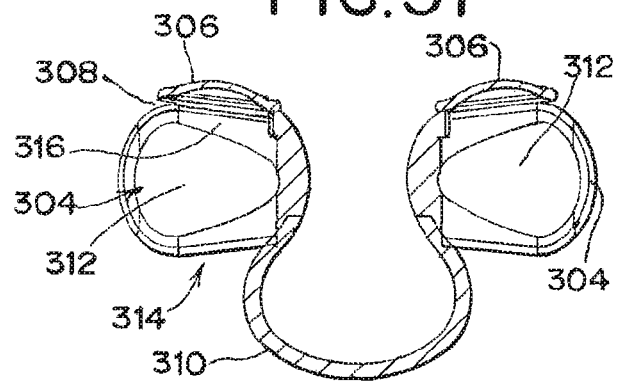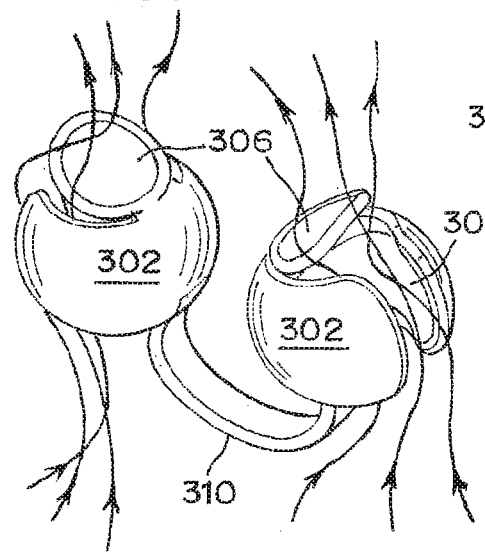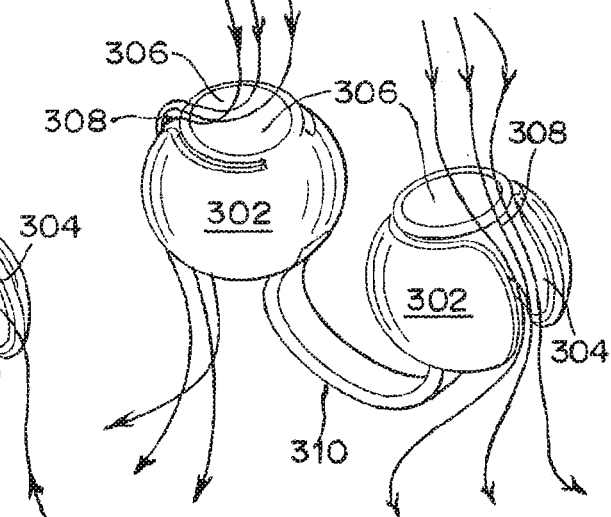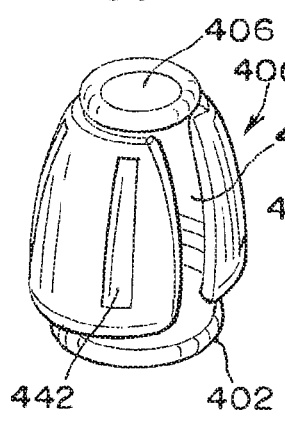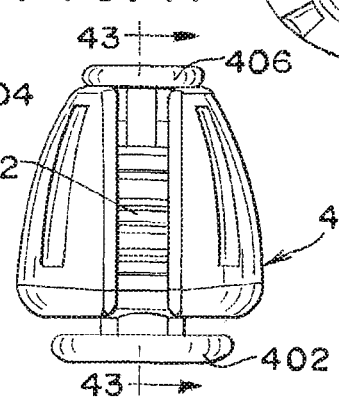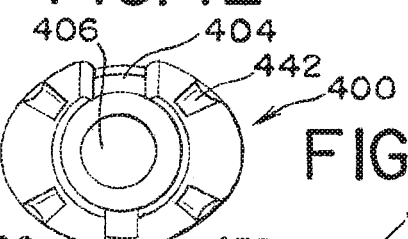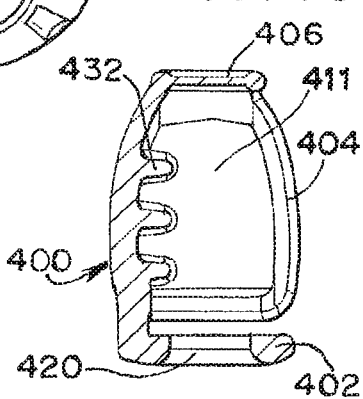

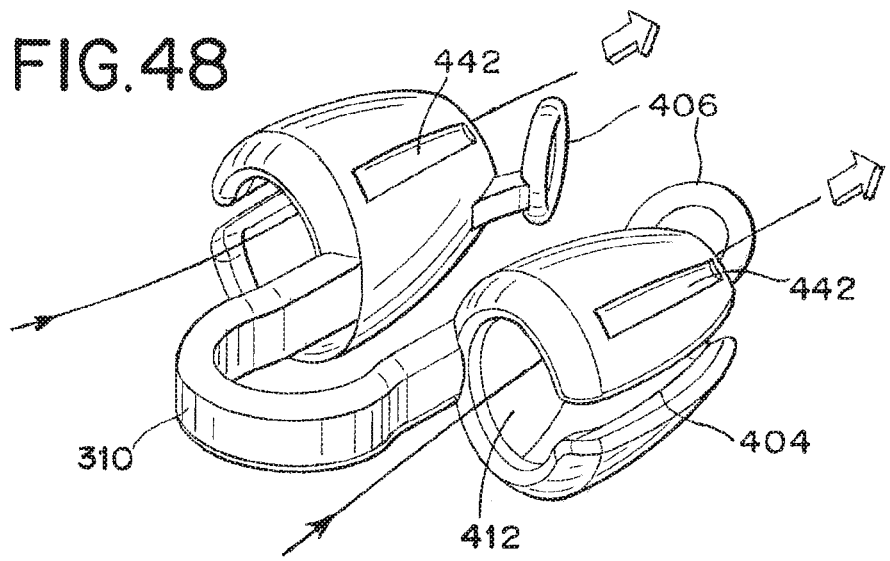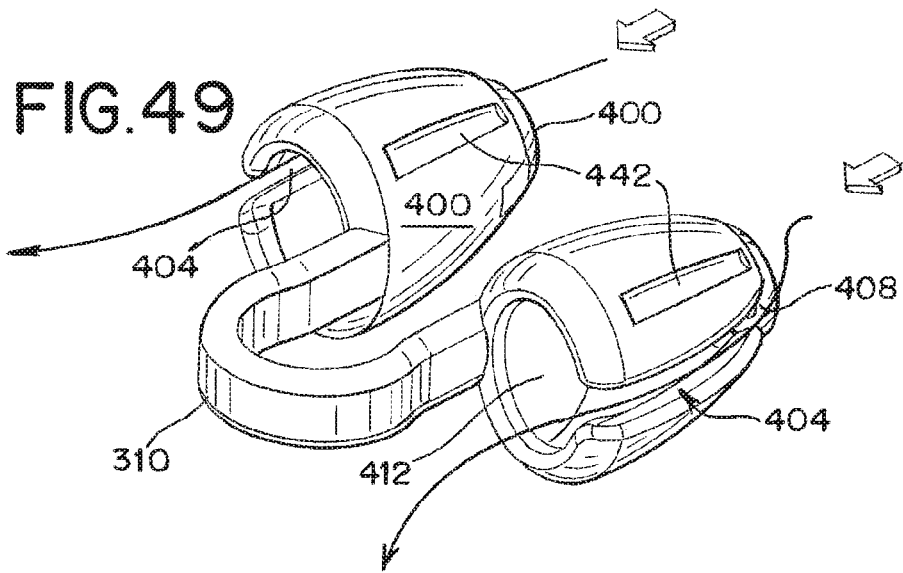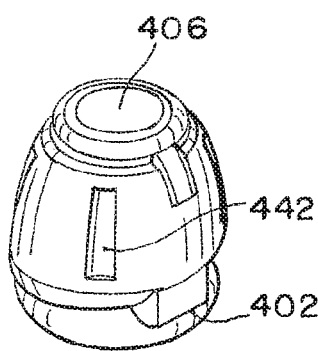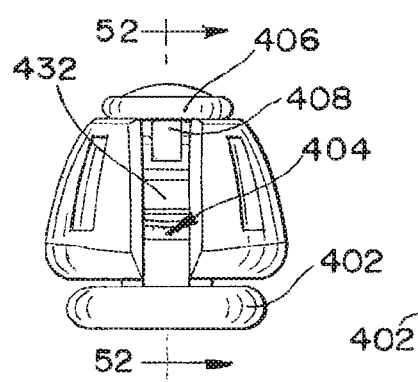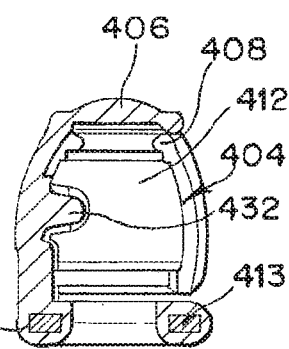

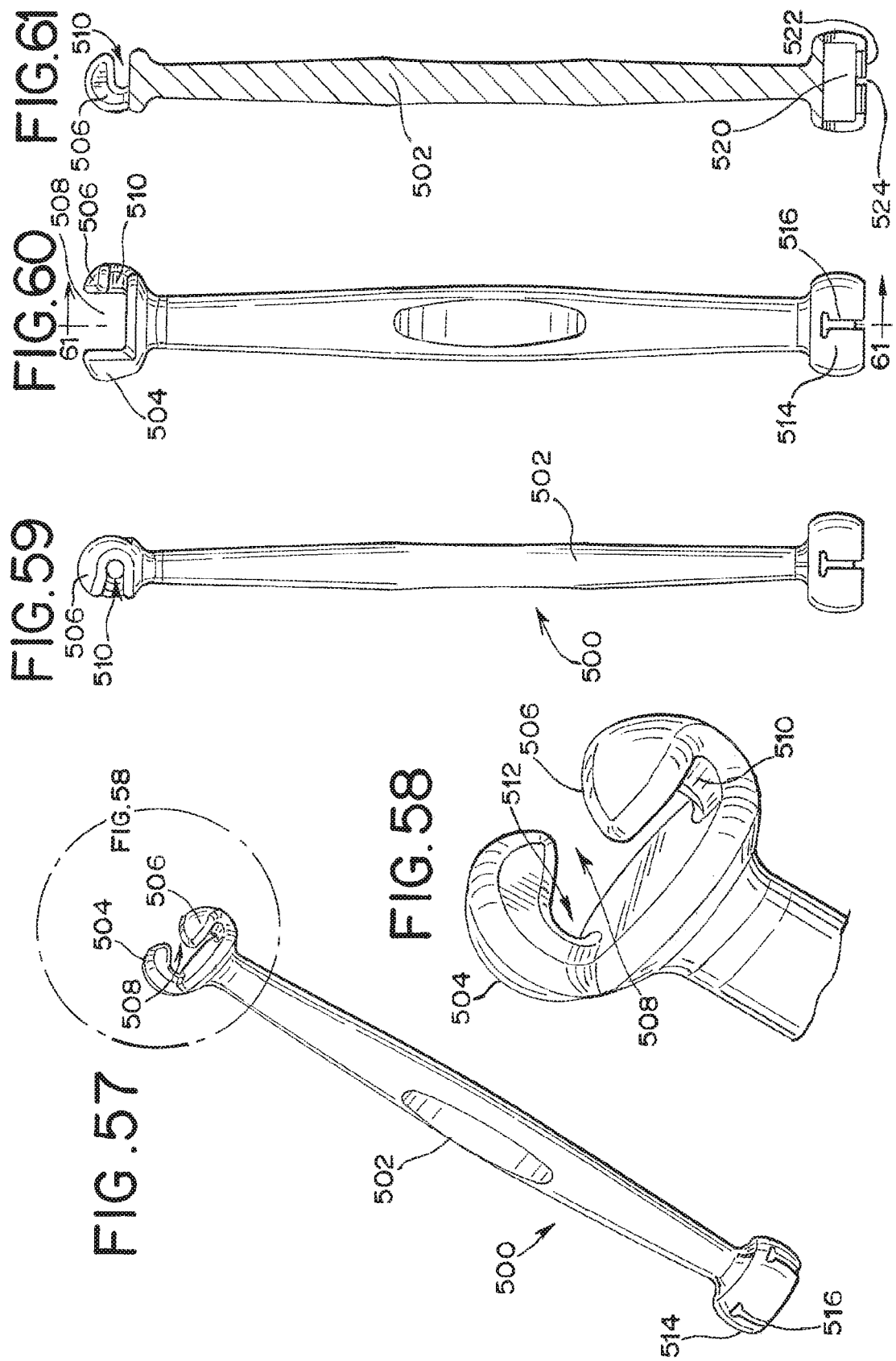

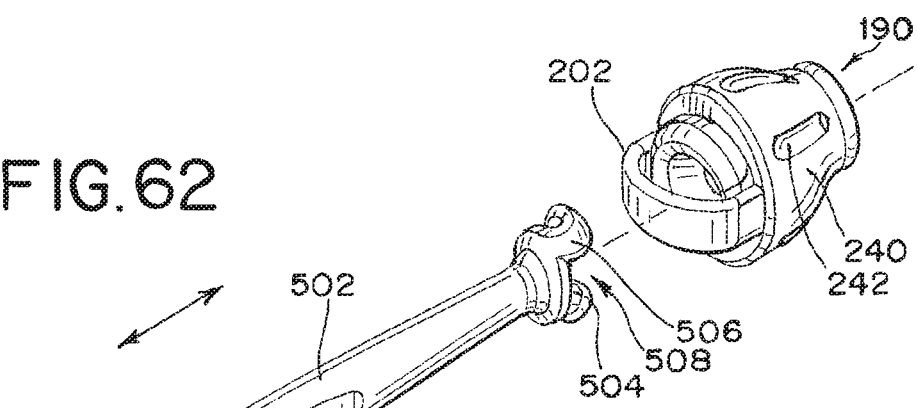
FIG. 62
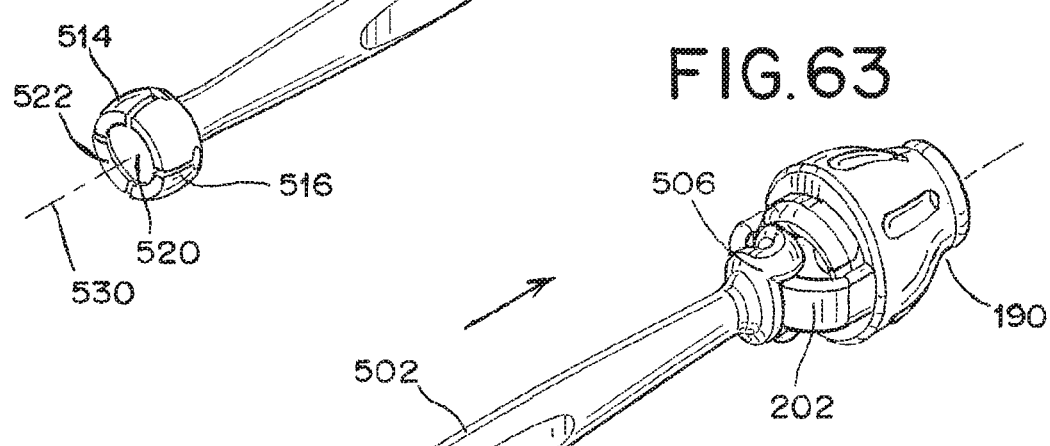
FIG. 63
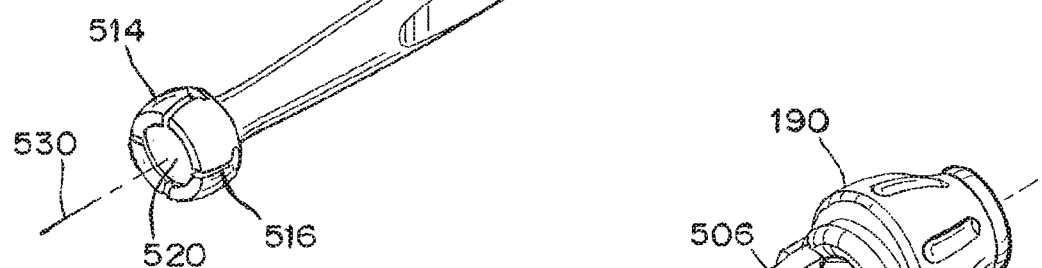
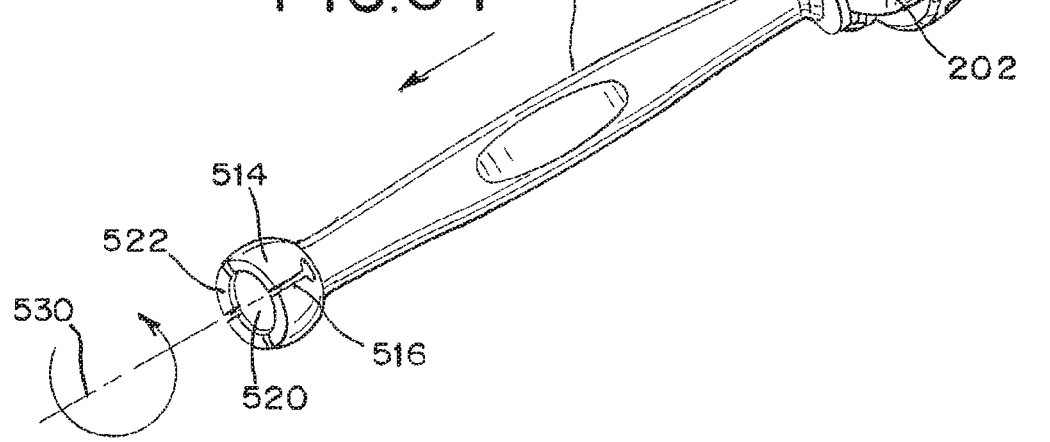
FIG. 64

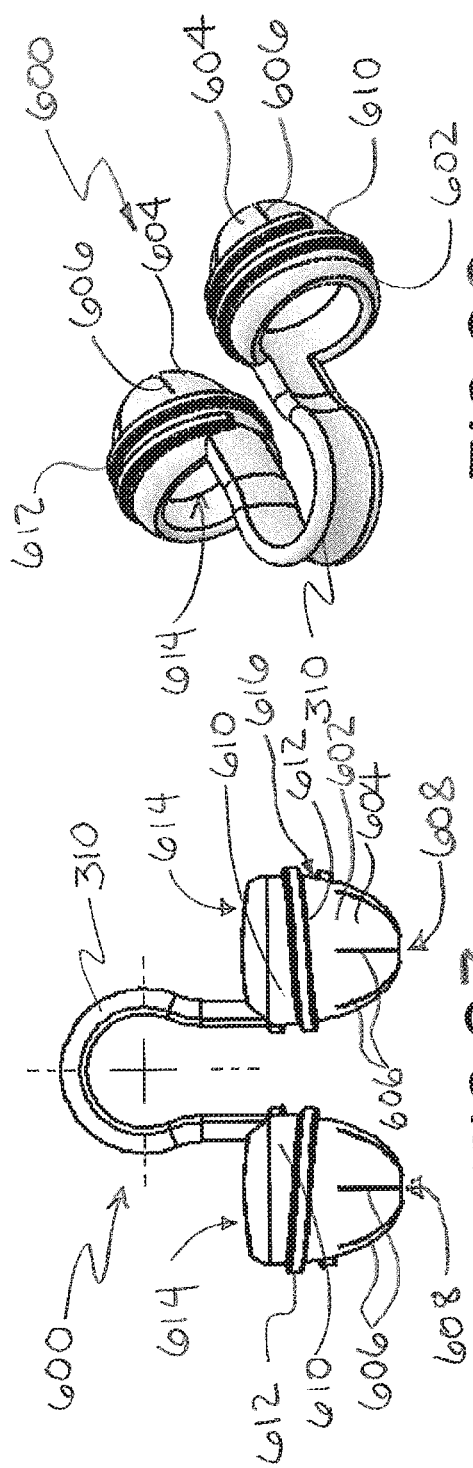
FIG.66
FIG.67
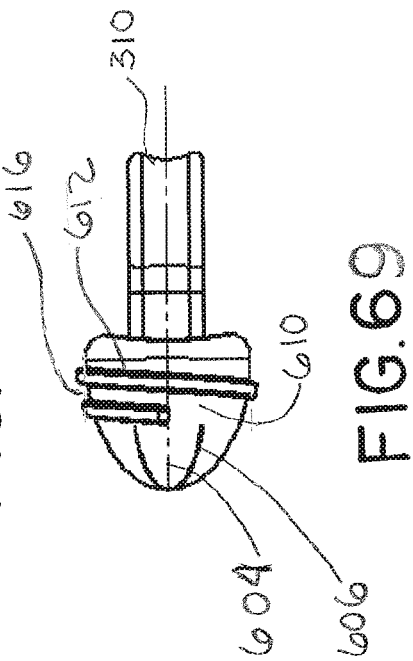
FIG.69
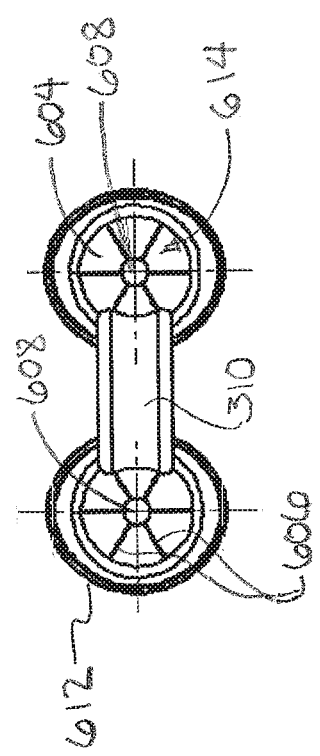
FIG.68

NASAL INSERT AND CANNULA AND METHODS FOR THE USE THEREOF

This application is a continuation of U.S. application Ser. No. 13/629,921, filed Sep. 28, 2012, which claims the benefit of U.S. Provisional Application No. 61/540,740, filed Sep. 29, 2011, entitled "Nasal Insert and Cannula and Methods for the Use Thereof," the entire disclosures of which are hereby incorporated herein by reference.

TECHNICAL FIELD

The present invention relates generally to a nasal insert, and in particular, to a nasal insert and cannula suitable for the treatment of various sleep disorders, including without limitation sleep apnea.

BACKGROUND

There are a wide variety of different diseases and physiological disorders associated with breathing, including sleep disorders such as sleep apnea and snoring, chronic obstructive pulmonary disease (CPOD), bronchitis, asthma and others. Many of these diseases and disorders may be treated by modifying the respiratory cycle.

For example, various oral or dental devices, such as the mandibular advancement device (MAD), have been developed for sleep apnea, and may be effective for treatment of mild sleep apnea, especially for patients that sleep on their back or stomach, and may improve airflow for patients with severe sleep apnea. These types of oral/dental devices may not be as effective, however, as continuous positive airway pressure devices (CPAP). Moreover, oral/dental devices are typically expensive, and may be associated with various side effects, including nighttime pain, dry lips, tooth discomfort, rearrangement in tooth and jaw positions, and excessive salivation, one or more of which may lead to reduced patient compliance.

CPAP devices will effectively control sleep apnea, but patient compliance may again be low, due for example to the discomfort of, and claustrophobic feeling associated with, the mask, pressure of the device, noise associated with the machine, entanglement of tubes, etc.

Other devices, as disclosed for example and without limitation in U.S. Pat. No. 7,735,491 to Doshi, U.S. Pat. No. 6,626,179 to Pedley and WO 2007/134458 to Robitaille, have been developed to treat sleep apnea and other respiratory disease and disorders by interfacing with the nasal passage of the user. Many of these types of nasal insert devices, however, may be difficult to properly install and/or use, for example requiring screwing of the device into the nasal passageway. In other systems, a holdfast, which secures the device to the user, may be external to the user, leading to lower levels of comfort and compliance. Conversely, internal holdfast systems may have a limited size variance, leading to such devices being either too tight or too loose, and/or adversely affecting the comfort level of the device and the associated compliance. Indeed, internal holdfast systems are often intended to create a tight seal with the nasal passageway, which may limit the population associated with any particular device.

SUMMARY

Briefly stated, in one aspect, one embodiment of a nasal insert includes a housing having a circumferential wall defining an interior passage. The wall has a longitudinal gap extending along a length thereof, with an outer peripheral dimension of the housing being adjustable by varying the gap. A valve is in communication with the interior passage and limits a fluid flow through the interior passage in at least one direction.

In another embodiment, a nasal insert includes a user interface having a tubular housing defining an interior cavity open at opposite ends. An exterior surface of the housing is adapted to interface with a nasal vestibule of a user. A base is received in the interior cavity of the housing and includes an exit port. A cap is connected to the base and has an input port. A valve member is disposed in an interior passage defined by at least one of the cap and base, with the valve member being moveably received in the interior passage.

In yet another aspect, an embodiment of a nasal insert includes a housing including an interior passageway having a polygonal cross-section and a valve member disposed in the interior passageway. The valve member is moveably received in the interior passage and has a different cross-sectional shape than the polygonal cross-section. At least one airflow passageway is formed between the valve member and the interior passageway.

In another embodiment, a nasal insert includes a housing having a longitudinally extending flow passageway and an opening formed in a side thereof transversely to the flow passageway. A valve member is inserted into the flow passageway through the opening. A user interface is disposed around the housing and covers the opening so as to retain the valve member in the flow passageway. In one embodiment, a panel may be provided to cover the opening before the user interface is disposed around the housing.

Various methods of providing resistance during exhalation are also provided. For example, in one embodiment, a method of providing resistance during exhalation includes providing a housing having a circumferential wall defining an interior passage, wherein the wall has a longitudinal gap extending along a length thereof. The method includes squeezing the housing and thereby closing at least a portion of the gap, inserting the housing into a nasal passage of a user while the housing is being squeezed and releasing the housing and thereby letting the gap increase as the housing expands into the nasal passage of the user. The method further includes inhaling through the housing and passing air through a valve in communication with the interior passage and exhaling through the housing and limiting a flow of exhaled air through the interior passage with the valve while passing at least a portion of the exhaled air through the gap.

In another embodiment, a method of providing resistance during exhalation includes compressing a user interface having an exterior tubular housing, inserting the user interface into a nasal passage of a user while the user interface is being compressed, and releasing the user interface and thereby letting the user interface expand into the nasal passage of the user. The method further includes inhaling through an interior housing disposed in the exterior tubular housing, wherein the interior housing is less compressible than the exterior housing and passing air through a valve disposed in the interior housing. The method further includes exhaling through the interior housing and limiting a flow of exhaled air through the interior housing with the valve.

In another aspect, a method of assembling a nasal insert includes inserting a valve member through an opening in the side of a housing, wherein the housing has a longitudinally extending flow passageway, and disposing a user interface around the housing and thereby covering the opening with the user interface so as to retain the valve member in the flow passageway.

The various aspects and embodiments provide significant advantages over other nasal inserts. For example and without limitation, a nasal insert configured with a gap may be easily inserted into a wide population of users with different size nasal passageways. At the same time, the gap provides a defined passageway for the flow of air. In addition, an embodiment configured with a base and cap allows for secure disposal of the valve member, thereby avoiding aspiration into the user's lungs, while providing for a simple and robust design. At the same time, the interface between the valve member and passageway provides for predetermined air flow paths and associated amounts of resistance.

The present invention, together with further objects and advantages, will be best understood by reference to the following detailed description taken in conjunction with the accompanying drawings.

BRIEF DESCRIPTION OF THE DRAWINGS

FIG. 1 is a perspective view of a first embodiment of a nasal insert assembly.

FIG. 2 is a top view of the nasal insert shown in FIG. 1.

FIG. 3 is an end view of the nasal insert shown in FIG. 1.

FIG. 4 is an exploded perspective view of the nasal insert shown in FIG. 1.

FIG. 5 is a cross-sectional view of the nasal insert taken along line 5-5 of FIG. 3 during inhalation.

FIG. 6 is a cross-sectional view of the nasal insert taken along line 6-6 of FIG. 3 during exhalation.

FIG. 7 is an end view of one of the nasal inserts.

FIG. 8 is an enlarged partial cross-sectional view of the nasal insert taken along line 8 of FIG. 6.

FIG. 9 is an enlarged partial view taken along line 9 of FIG. 7.

FIG. 10 is a front view of a nasal cannula assembly.

FIG. 11 is a cross-sectional view taken along line 11-11 of FIG. 10.

FIG. 12 is an alternative embodiment of nasal insert assembly.

FIG. 13 is a side view of the nasal insert assembly shown in FIG. 12.

FIG. 14 is a perspective view of an alternative embodiment of a nasal cannula assembly.

FIG. 15 is a perspective view of an alternative embodiment of a nasal insert.

FIG. 16 is a side view of the nasal insert shown in FIG. 15.

FIG. 17 is an end view of the nasal insert shown in FIG. 15.

FIG. 18 is a cross-sectional view of the nasal insert shown in FIG. 15 during inhalation.

FIG. 19 is a cross-sectional view of the nasal insert shown in FIG. 15 during exhalation.

FIG. 20 is a cross-sectional view of an alternative embodiment of a nasal insert assembly.

FIG. 21 is an end view of the nasal insert assembly shown in FIG. 20.

FIG. 22 is a side view of the nasal insert assembly shown in FIG. 20.

FIG. 28 is a perspective view of an alternative embodiment of a nasal insert.

FIG. 29 is a first side view of the nasal insert shown in FIG. 28.

FIG. 30 is a second side view of the nasal insert shown in FIG. 28.

FIG. 31 is a cross-sectional view of the nasal insert taken along line 31-31 of FIG. 29.

FIG. 32 is an exploded view of the nasal insert shown in FIG. 28.

FIGS. 33A-C are three perspective views of the nasal insert shown in FIG. 28.

FIG. 34 is a perspective view of an alternative embodiment of a nasal insert assembly.

FIG. 35 is a top view of the nasal insert assembly shown in FIG. 34

FIG. 36 is a side view of the nasal insert assembly shown in FIG. 34.

FIG. 37 is a cross-sectional view of the nasal insert assembly taken along line 37-37 of FIG. 36.

FIG. 38 is a perspective view of the nasal insert assembly shown in FIG. 34 during inhalation.

FIG. 39 is a perspective view of the nasal insert assembly shown in FIG. 34 during exhalation.

FIG. 40 is a perspective view of an alternative embodiment of a nasal insert.

FIG. 41 is a side view of the nasal insert shown in FIG. 40.

FIG. 42 is an end view of the nasal insert shown in FIG. 40.

FIG. 43 is a cross-sectional view of a nasal insert taken along line 43-43 of FIG. 41.

FIG. 48 is a perspective view of a nasal insert assembly during inhalation.

FIG. 49 is a perspective view of a nasal insert assembly during exhalation.

FIG. 50 is a perspective view of an alternative embodiment of a nasal insert.

FIG. 51 is a side view of the nasal insert shown in FIG. 50.

FIG. 52 is a cross-sectional view of a nasal insert taken along line 52-52 of FIG. 51.

FIG. 57 is a perspective view of an insertion/extraction device.

FIG. 58 is an enlarged end view of the insertion/extraction device shown in FIG. 57.

FIG. 59 is a side view of the insertion/extraction device shown in FIG. 57.

FIG. 60 is a front view of the insertion/extraction device shown in FIG. 57.

FIG. 61 is a cross-sectional view of the insertion/extraction device shown in FIG. 57 taken along line 61-61.

FIG. 62 is a perspective view of the insertion/extraction device prior to engagement with a nasal insert.

FIG. 63 is a perspective view of the insertion/extraction device disposed relative to a nasal insert for engagement therewith.

FIG. 64 is a perspective view of the insertion/extraction device engaged with a nasal insert.

FIG. 66 is a perspective view of an alternative embodiment of a nasal insert assembly.

FIG. 67 is a top view of the nasal insert assembly shown in FIG. 66.

FIG. 68 is an end view of the nasal insert assembly shown in FIG. 66.

FIG. 69 is an side view of the nasal insert assembly shown in FIG. 66.

DETAILED DESCRIPTION OF THE PRESENTLY PREFERRED EMBODIMENTS

Figure 23:
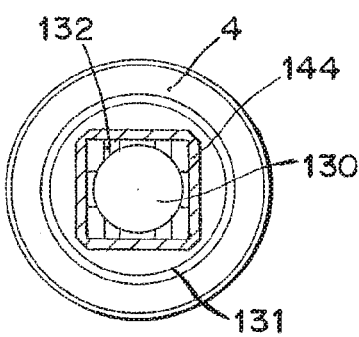
FIG. 23 is a cross-sectional view of a nasal insert taken along line 23-23 of FIG. 22.

Referring to the drawings, various nasal inserts, nasal insert assemblies and nasal cannula assemblies are shown. The phrase "nasal insert" and "nasal insert assembly" refer to a nasal insert configured to interface with one or both nasal cavities of the user, or in a cavity formed in the user's tracheotomy. The phrase "nasal cannula" of "nasal cannula assembly" refers to a nasal insert or assembly coupled to a delivery tube configured to deliver oxygen or other gases.

The terms "longitudinal" and "axial" as used herein relates to a length or lengthwise direction, including for example generally the direction of flow of fluids through the nasal inserts and assemblies. The term "lateral" and variations thereof refer to a sideways direction. The terms "top" and "bottom" are intended to indicate directions when viewing the nasal insert when positioned for insertion into the nasal cavity of the user, with the "top" end thereof being inserted first. However, it should be understood that a user can use the nasal insert and assembly, and cannula assembly, when the user is in any number of positions, including but not limited to an upright position (seated or standing) or horizontal position (whether lying sideways, prone or supine).

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. The term "transverse" means extending across an axis, including without limitation substantially perpendicular to an axis. It should be understood that the use of numerical terms "first," "second," "third," etc., as used herein does not refer to any particular sequence or order of components; for example "first" and "second" housing members may refer to any sequence of such members, and is not limited to the first and second indicator members of a particular configuration unless otherwise specified. It should be understood that the terms "input port" and "exit port" refer to the function of the ports during an inhalation phase, and that those same ports serve the opposite function (input and exit) during an exhalation phase.

Referring to FIGS. 1-9, one embodiment of a nasal insert 2 is shown as including a user interface 4 comprising a tubular housing defining an interior cavity 6 open at opposite ends. The user interface 4 has an exterior surface 8 adapted to interface with a nasal vestibule of a user. In one embodiment, the nasal insert is made of a compressible material, such as foam, and includes a plurality of annular ribs 10 as shown in FIGS. 1 and 2. The ribs may be more easily compressed and/or deflected, such that the nasal tissue is allowed to settle in between the ridges/ribs and help to maintain the nasal insert in the nasal cavity. Alternatively as shown in FIG. 4, the user interface 4 has a smooth and continuous exterior surface 8, with the interface 4 being compressed and then expanding against the walls of the nasal cavity to maintain the position of the nasal insert in the cavity.

Figure 65:
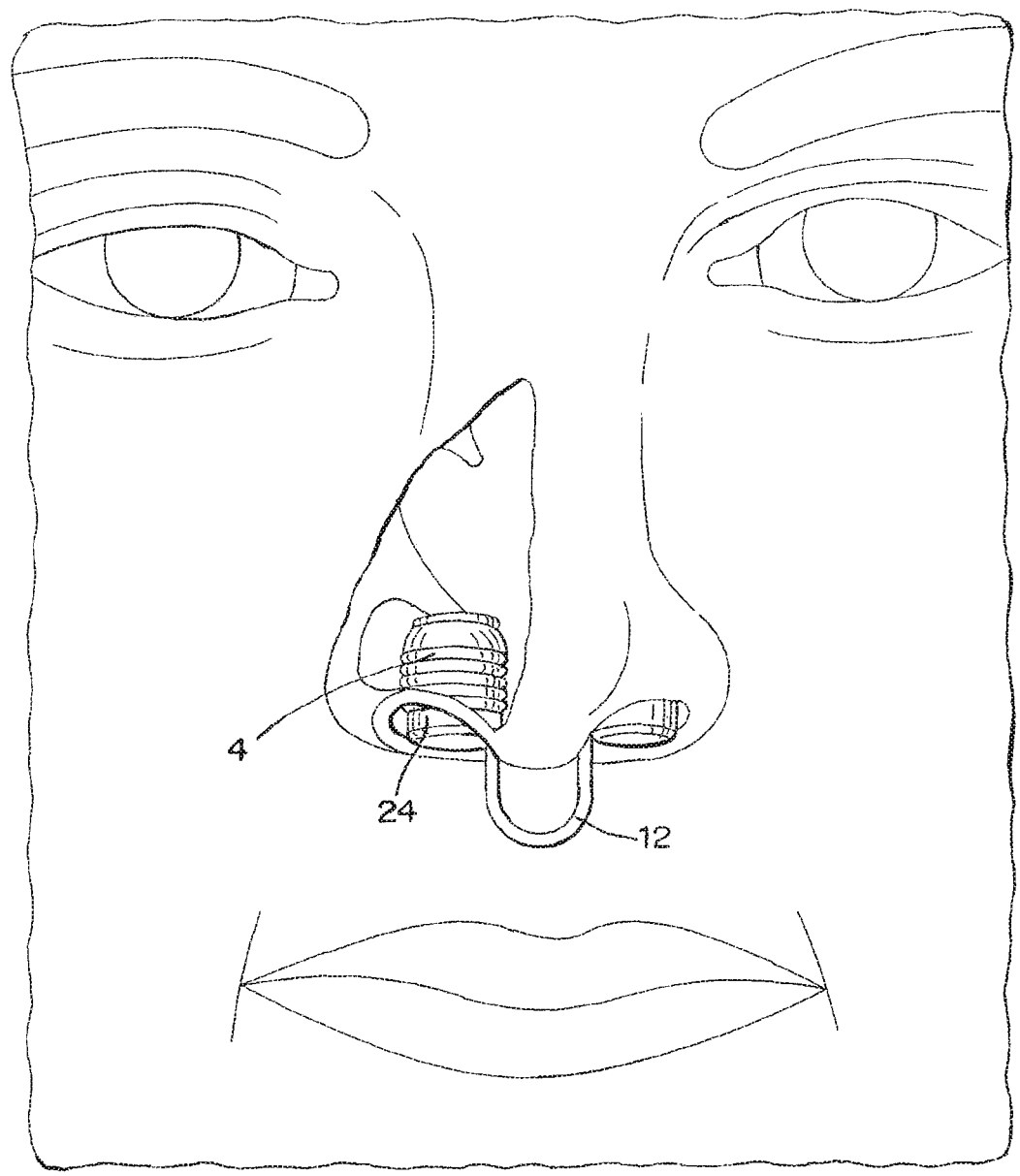
FIG. 65 is a front view of a nasal insert assembly applied to a user.

The nasal insert 2 may be configured as a single unit, which is suitable for independent and separate insertion into a single nasal cavity of the user or tracheomoty, or may include a pair of units, connected with a bridge 12, which are configured for insertion into adjacent nasal cavities of the user as shown for example in FIG. 65. It should be understood that other embodiments described and shown herein may be inserted, or installed, in a similar manner. In various embodiments, the bridge 12 may be configured as a resilient strap in a U-shape, such that it does not interfere with the user's nose. The bridge 12 may be grasped for inserting and extracting the nasal inserts 2 from the nasal cavities. In other embodiments, the bridge may be configured as a tether.

The nasal insert 2 further includes a base 50 that is shaped to be received in the interior cavity 6 of the user interface housing. The base 50 defines and includes an exit port 52. A cap 24 is connected to the base and defines and includes an input port 54. The base and cap are configured to fit together, with one or both of the base and cap, alone or in combination, defining an interior passageway 40. A valve member 30 is moveably disposed in the interior passage. As shown in FIG. 5, the bridge 12 may be formed integrally with the base 50, or alternatively with cap 24, with the base or bridge having a catch or tab 14 that is received in a groove or recess 16 formed on an interior of the user interface housing 4 so as to secure and prevent relative longitudinal movement of the cap/base and user interface.

As shown in FIGS. 4-6, an insert end 18 of the base narrows, whether by tapering or curvature, relative to an opposite end 20 secured to the cap 24, so as to form a neck. In this way, the user interface 4, which fits as a collar around the neck, may be compressed to a greater degree at the insert end. Preferably, the base is made of a less compressible material than the user interface. The various components may be made of medical grade plastics appropriate for the different application and which are approved by the FDA. For example, the base may be made from a variety of engineering thermoplastics including without limitation polycarbonate, polyphenylene, polyethylene or polypropylene. The user interface may be made of rubber, foam or the like, or combinations thereof, including without limitation low density polymers, polyurethane elastomers or synthetic silicone. The insert end 18 of the base may be configured with a rim 22, which engages and retains the user interface 4 around the base.

In one embodiment, the cap 24 includes a baffle 26 defining a plurality of valve openings 28, shown as three, arranged around a central opening 36. It should be understood that the baffle may be formed on the base, or separately formed and coupled between the base and cap. In one embodiment, best shown in FIGS. 7-9, the valve openings 28 have substantially a kidney bean shape, with an interior edge 29 being substantially linear or with a slight curve or large radius. In this way, the valve member 30, which abuts against the baffle (acting as a valve seat), is prevented from closing entirely the valve openings during exhalation, thereby providing a bleed opening 32 that provides continuous resistance to the exhaled air flow, which creates in turn a positive pressure in the airways to prevent airway tissue from obstructing the breathing passageway of the user. For example, the back of the tongue muscle may rest against the soft palate, and both against the oral pharynx. In another example, when the patient is lying on their back and asleep, the side walls may fall together to narrow or close the airway. When the muscles of breathing work to expand the chest and lower the diaphragm to draw in a breath of air, a negative pressure is generated that literally sucks the tissue together. The positive pressure in the airway created by the nasal insert assembly during exhalation prevents the tissues from making contact and being sucked together during inhalation. Instead, the tissues expand away from each other, with the apnea and snoring thereby being greatly reduced. At the same time, the bleed openings 32 provide for an escape passageway for oxygen when the nasal insert is coupled to a gas supply in a nasal cannula configuration, as further explained below. The bleed passageways also create a safety feature that provides a constant leak during exhalation.

In one embodiment, the valve member 30 is configured as an O-ring, which moves reciprocally in the passageway 40 defined by the cap 24 and base 50. In one embodiment, the valve member surrounds and is moveable along a hub 48, which is configured with three fingers in one embodiment and forms part of the baffle 26. The three fingers help control and maintain the alignment of the O-ring valve member along a centerline of the assembly. In an inspiration position, shown in FIG. 5, the valve member 30 is abutted against a stop 42, but does not seal against the stop, such that gas, including for example and without limitation air, may flow freely to the user through the exit port 52 during inhalation. In addition, the central passageway 36 is formed through the hub 48 defining the baffle. The central passageway 36 remains open at all times during both inhalation and exhalation. In one embodiment, the central opening 36 has a diameter of about 1 mm, while in other embodiments, the opening may have a diameter of 1.2 mm to 1.6 mm. During inhalation, due to the central passageway 36 and the openings 28, which are not blocked by the valve member, less than or about 1 cm of water resistance is generated during inhalation.

During exhalation as shown in FIGS. 6-9, the valve member 30 moves toward the seat 26 and partially closes or blocks the openings 28 leaving only the bleed openings 32 uncovered, together with the central passageway 36, thereby creating a positive pressure within the airways of about 5 to 20 cm. of water, and in one embodiment between about 5 and 15 cm.

The cap 24 and base 50 are coupled together, for example with a snap fit. As shown in FIGS. 4 and 15-19, the base may have a pair of resilient arms 58 that interface and slide along a pair of recesses 60 until the arms are engaged with the cap by way of a snap fit, with the base having an outer annular skirt 62 overlapping an inner annular skirt 64 of the cap. Of course, the overlap may be reversed. The user interface is then disposed over one or both of the cap and base, and may further secure, or maintain the coupling between, those components one to the other. The user interface 4 may be secured by way of friction, or with adhesives or other fasteners such as the tab 14 and recess 16 interface or rim 22.

Referring to the embodiment of FIGS. 10 and 11, the nasal insert may be coupled to a cannula 70 so as to deliver a gas such as oxygen. In this embodiment, the cap includes an insert portion or prong 72 defining a central opening 74 therethrough, which opening 74 is in fluid communication with the central opening 36 passageway of the baffle. The prong 72 extends outwardly from the cap 24 and has an exterior surface 80 with a shape, such as a tapered frusto-conical shape or a tubular shape, configured to be received in an inlet tube 76 of the nasal cannula, which further communicates with a manifold tube 86. A supply tube 90, or a pair thereof, may then be coupled to opposite ends of the manifold. Conversely, the insert portion 72 may have an inner diameter sized and shaped to receive the inlet tube 76. In either embodiment, an opening 92 is formed around the outside of the tube and insert such that ambient air may also be inhaled through the nasal insert. In this way, a continuous flow of oxygen during inhalation and exhalation may be maintained without any restriction to the oxygen gas flow.

In an alternative embodiment, shown in FIGS. 12-14, the bridge also serves as a clip having a pair of resilient arms 100 with curved clamping members 102, which may be secured to a cannula. Again, the nasal insert may be configured with an insert portion. The clip may be in-molded with the base, or separately configured and attached to the base and/or cap. The arms 100 may be biased away from each other as a manifold 88 is inserted between the clamping members 102, with the arms 100 then being released to secure the nasal insert to the manifold.

In an alternative embodiment, shown in FIGS. 20-24, a valve member 130 is configured as a ball. In this embodiment, a housing 131 defines the interior passageway 132, which is configured with a polygonal cross-section, including for example and without limitation as a triangle, rectangle (including square), diamond, hexagon, pentagon, octagon, etc. In this way, the ball shaped valve member 130 is not allowed to completely seal the passageway 132 as air flows around the ball at the corners of the adjoining walls defining the interior cross-section of the passageway. The housing 131 may be may a single piece, or may be configured with a base and cap. At an outlet end 134 to the passageway, there is a minimal amount of resistance during inhalation due to the configuration of the valve seat 136 interfacing with the valve member, with the valve seat including a plurality of stops 144. At the inlet end 138, a circular opening 140 is presented in the passageway. The ball shaped valve ember 130 is prevented from closing the opening in the passageway by a plurality of bars or stops 142 which define a valve seat. The length of the stops 142 determines the resistance of air flow by setting the distance between the ball 130 and the circular opening 140. The less space, the greater the resistance and an associated pressure in the upper airways of the user.

Referring to FIGS. 20-27, the outlet end 134 may have more substantial stops 144 or indents that prevent the ball from sealing the passageway, and thereby allow for minimum resistance to air flow. At the inlet end 138, the stops 142 are shorter, or have a lesser extent, such that the ball 130 may move closer to the opening 140 and thereby create a greater resistance, and higher pressures in the upper airways during exhalation. In one embodiment, the stops 144 are permanently fixed at the outlet end, while at the inlet end the length or amount of protrusion of the stops 142 may be variable, for example by screwing a valve seat longitudinally in or out, by moving the valve seat against the force of friction, by fixing the position thereof with detents, or by rotating the stops 142 with a ratchet type device or other tool. In this way, the valve member 130 moves reciprocally in opposite first and second directions I and E in response to the flow inhalation and exhalation flows If and Ef in response to inhalation and exhalation by a user, with the valve member engaging a first valve seat 144 when moved in the first direction in response to the user inhalation, and wherein the valve member engages a second valve seat 142 when moved in the second direction in response to the user exhalation. The first and second valve seats 144, 142 are configured such that the valve member 130 creates a greater resistance to air flow during the user exhalation than during the user inhalation.

Figure 24:
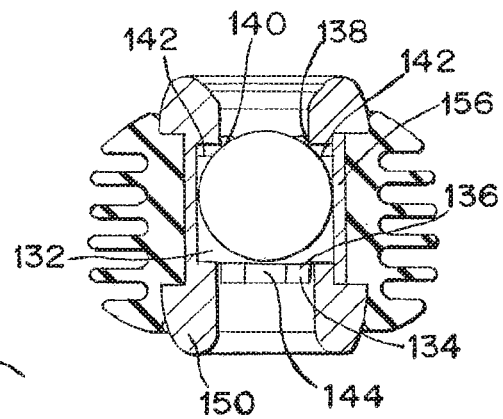
FIG. 24 is a cross-sectional view of a nasal insert.
Figure 25:
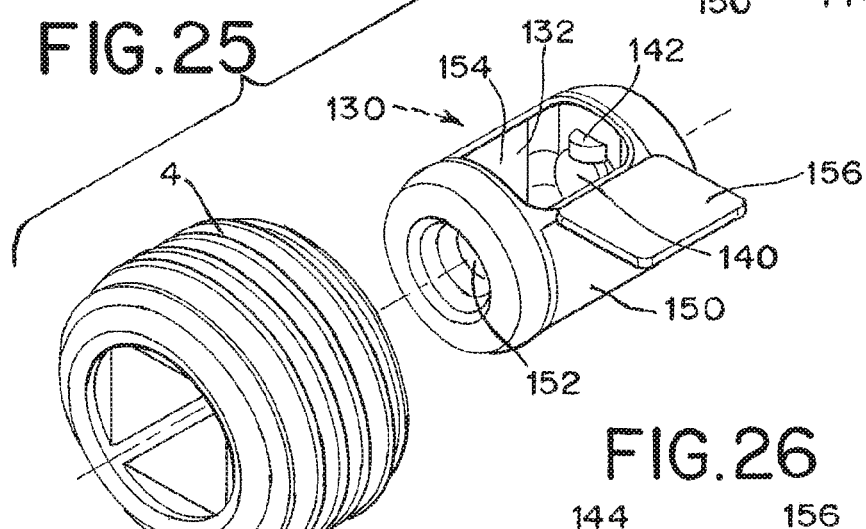
FIG. 25 is an exploded view of one embodiment of a nasal insert.
Figure 26:
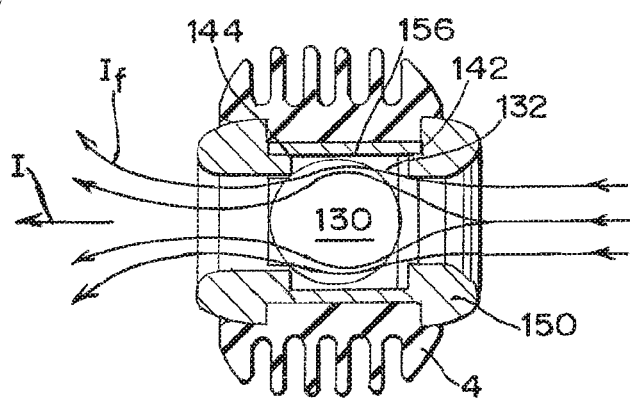
FIG. 26 is a cross-sectional view of the nasal insert shown in FIG. 24 during inhalation.
Figure 27:
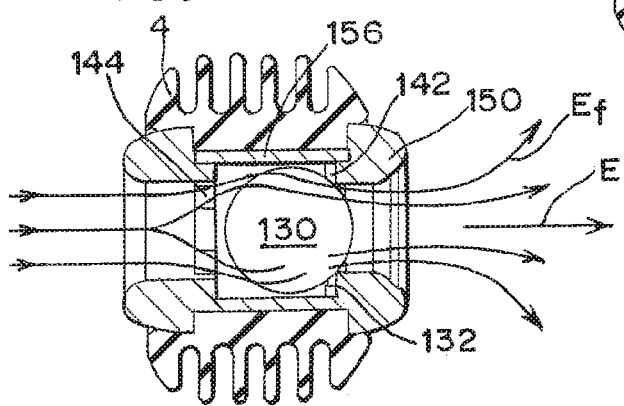
FIG. 27 is a cross-sectional view of the nasal insert shown in FIG. 24 during exhalation.
Figure 44:
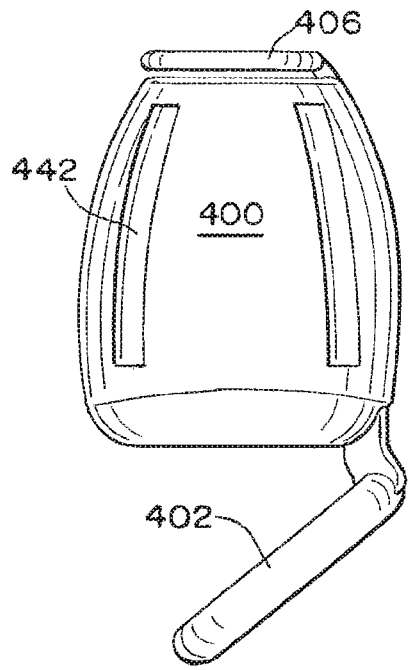
FIG. 44 is a side view of the nasal insert shown in FIG. 40 during extraction.
Figure 45:
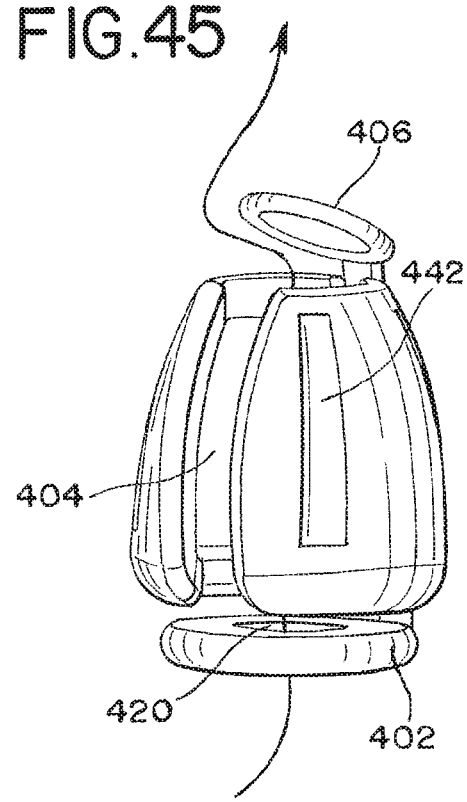
FIG. 45 is a perspective view of the nasal insert shown in FIG. 40 during inhalation.

Referring to FIG. 24, a single insert may be used for a tracheotomy and/or an endotracheal tube. The openings at the opposite ends of the passageway may be about 15 mm. In one embodiment, the an outside diameter at the outlet opening is 15 mm OD, while the cap has an inlet opening with a 15 mm inner diameter, such that the assembly may be coupled to an endotracheal tube or tracheotomy tube. In some embodiments, the openings at the opposite ends of the passageway may be about 8 mm to about 10 mm in diameter.

In one embodiment, shown in FIGS. 24-27, a housing 150 is formed as a single homogenous unit defining a longitudinal passageway 152, with an access opening 154 formed in a side of a housing transverse to the passageway. A panel 156, shown as a hinged door, may be moved from an open to a closed position. During assembly, the panel 156 is opened and the valve member 130, shown as a ball, is inserted transversely through the access opening 154. The panel 156 is then closed, with the user interface 4 then being disposed over the housing 150 to secure the panel in place. The valve member 130 reciprocally moves in a longitudinal direction within the passageway 152. Again, stops 142, 144 may be positioned at opposite ends of the passageway adjacent the openings 140 to provide a differential resistance upon inhalation and exhalation. In one embodiment, the stop at the inlet end may be fixed or varied between 0.01 mm to about 2 mm, or between about 0.01 mm to about 1.5 mm in other embodiments. The lesser the height, the greater the resistance to exhaled gases, and the greater the corresponding positive pressure achieved in the user's upper airway passage.

Referring to the embodiment shown in FIGS. 28-33C, a shorter insert 190, suitable for a user having smaller vestibule openings, is shown as including a base 200 with an elongated strap 202. During assembly, a valve member 130 is disposed in a cavity 204 formed in the end of the base. A cap member 206 is then secured to the base to trap or hold the valve member in an interior passageway, defined by the cavity 204. The strap 202 is then bent or curved around, such that a free end portion 208 thereof maybe secured to the base, for example by engaging a button 212 with a hole 210 in the end portion. It should be understood that any form of coupling, including a loop/insert, snap fit, adhesives, mechanical fasteners, etc. may also be suitable. A user interface 240 is then disposed over the base, and covers the free end of the strap to complete the assembly. The user interface has a plurality of exterior, longitudinally extending recesses 242, which form and define air vents, and also function as an interference fit with the nasal tissues. In this way, the strap provides a grippable handle 220 suitable for assisting in inserting and extracting the nasal insert into and out of the nasal cavity of the user. The cap 206 and base 200 may again be configured with stop members 142, 144 at each end of the passageway to provide predetermined resistances during inhalation and exhalation.

Referring to FIGS. 57-64, an insertion/extraction device 500 is shown. The insertion/extraction device maybe configured with an elongated handle 502 that can be gripped by a user or caregiver. One end of the handle is configured with a pair of spaced apart hooks 504, 506 defining a gap 508, with each hook having a curved portion forming a recess or groove 510, 512. The grooves 510, 512 open in the opposite direction. An opposite end of the handle is configured with a magnet 520. The end of the handle includes a housing 514 with slits 516. The housing defines a cavity. The slits 516 permit the housing walls to be expanded for insertion of the magnet 520. The housing further includes an end cover 522, with slits, configured as a lip or rim in one embodiment, which encapsulate the magnet. The cover is thin enough so as to allow a sufficient magnetic force to attract a metal component disposed on or in an adjacent, corresponding nasal insert.

In operation, and referring to FIGS. 63 and 64, the insertion/extraction device 500 can be used to insert and extract the various nasal inserts described herein. For example and without limitation, the handle 502 can be moved toward an insert 190 having a strap 202, with the strap disposed in the gap 508 between the hooks 504, 506. The handle 502 is then rotated about a longitudinal axis 530 such that the hooks 504, 506 engage the strap in their respective grooves 510, 512 as shown in FIG. 64. The handle 502 may then be manipulated to insert the nasal insert 190 into the vestibule. The handle 502 and nasal insert 290 may be rotated (e.g., counterclockwise) such that the nasal insert resides in a comfortable position in the vestibule. The handle 502 may then be rotated in the opposite direction (e.g., clockwise) so as to disengage the hooks 504, 506 from the strap 202, with the handle 502 then being moved away from the nasal insert 190. The insertion/extraction device may also be used to extract the nasal insert by engaging the strap 202 through rotation and then moving the handle 502 and connected nasal insert 190 away from the vestibule to effect an extraction.

The opposite end of the handle may also be used for insertion/extraction. For example, the magnet 520 may attract a nasal insert, which may then be manipulated and inserted into a vestibule. The handle 502 may then be twisted or turned to disengage the magnet 520. The nasal insert may be extracted by first engaging the handle 502 through a magnetic attraction with the nasal insert, with the handle 520 and insert then being moved away from the vestibule.

Referring to FIGS. 34-56, a nasal insert includes a housing 300, 400 comprising a circumferential wall defining an interior passage. In one embodiment, the insert is formed with a generally spherical shape having a diameter of from about 8 mm to about 16 mm, and in one embodiment from about 12 mm to about 16 mm. The housing may be made low density polymers. The wall is configured with a longitudinal gap 304, 404 or slit that extends along a length thereof, and thereby communicates between the interior passageway 312, 412 and an exterior of the housing. In one embodiment, the gap is less than about 0.5 mm wide. In other embodiments, the slit is between about 2 mm and 4 mm. The housing 300, 400 may be gripped and squeezed such that an outer peripheral dimension of the housing, measured about a cross-section of the housing in a plane perpendicular to a longitudinal axis, is adjustable by varying the gap 304. In this way, the open side wall of the insert allow for adjustment of the size of the housing such that the housing will fit in different size nasal vestibules.

A valve 306 is in communication with the interior passage 312. The valve 306 limits a fluid flow through the interior passage in at least one direction. In one embodiment, the valve 306 is configured as a hinged flap covering one end of the interior passage. As shown in FIGS. 34-39 and 53-55, the valve flap 306, 406 covers the inlet end 316 of the passageway, such that the 306 flap may open during inhalation and close during exhalation. During inhalation, the flap 306 opens and allow for gases to be inhaled with minimum resistance, with an opening having a diameter of about 5 to 5.4 mm, and in another embodiment about 1.2 mm. During exhalation, the flap 306 closes and the expired gases pass around the flap along the gap 304 through an exhalation opening 314, which creates resistance and back pressure in the upper airway passage of the user. The flap 306 and gap 304 form a small bleed opening 308 positioned just below the flap 306. The opening may be between about 0.3 mm and 0.5 mm, with the area about 1 $mm^2$ to about 2 $mm^2$.

As shown in FIGS. 34-39, 48, 49 and 53-56, a bridge member 310 may connect a pair of nasal inserts at an end thereof opposite the hinged flap, with the bridge forming a grippable handle that facilitates insertion and extraction of the inserts. The bridge may include, or be made of a metal or hard plastic insert, which provides stability for the housing. The bridge may also be configured with a cannula clip as described above. The housing may have a substantially spherically shaped exterior, a frusto-conically shaped exterior, a cylindrically shaped exterior, or be otherwise shaped to interface with the nasal vestibule of the user. In one embodiment, a spherically shaped housing has an exterior surface with a radius of about 8 mm. In these embodiments, the flap 306 is substantially round.

Figure 46:
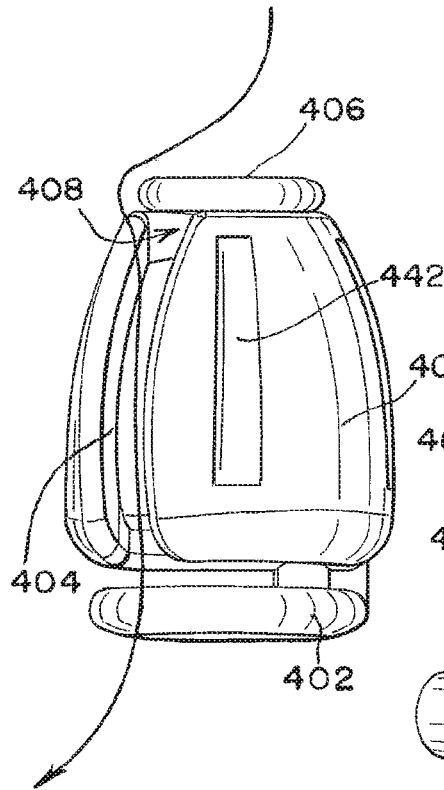
FIG. 46 is a perspective view of the nasal insert shown in FIG. 40 during exhalation.
Figure 47:
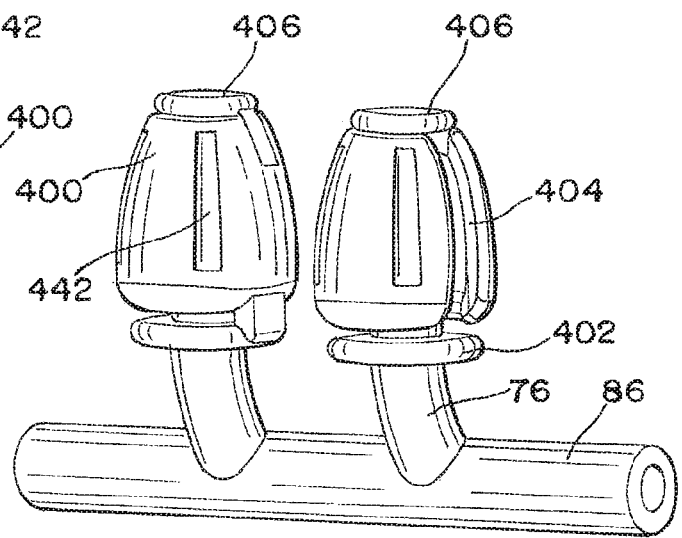
FIG. 47 is a perspective view of a nasal cannula assembly.
Figure 53:
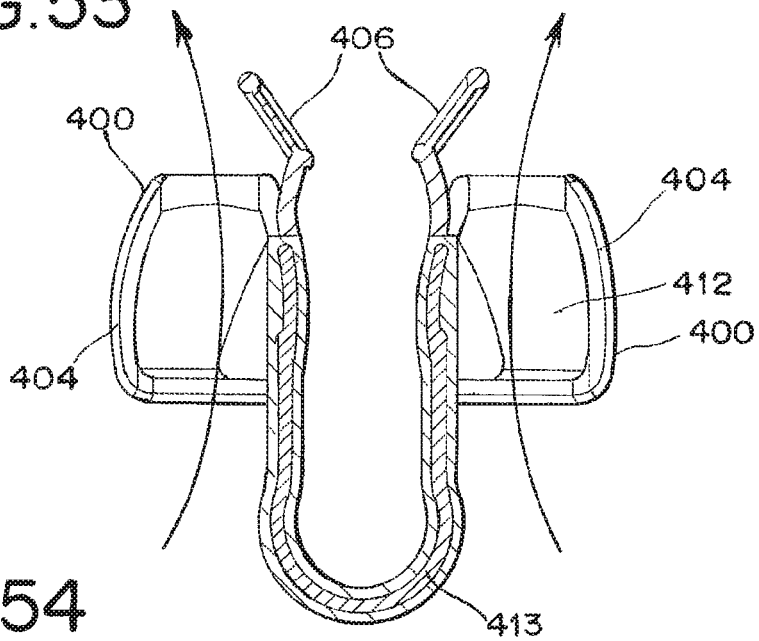
FIG. 53 is a cross-sectional view of alternative embodiment of a nasal insert during inhalation.
Figure 54:
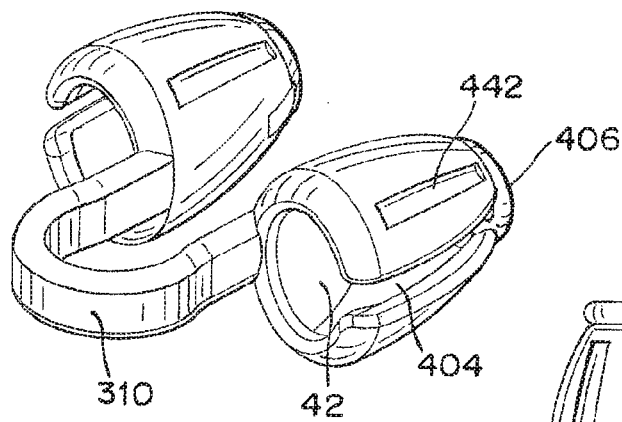
FIG. 54 is a perspective view of an alternative embodiment of a nasal insert assembly.
Figure 56:
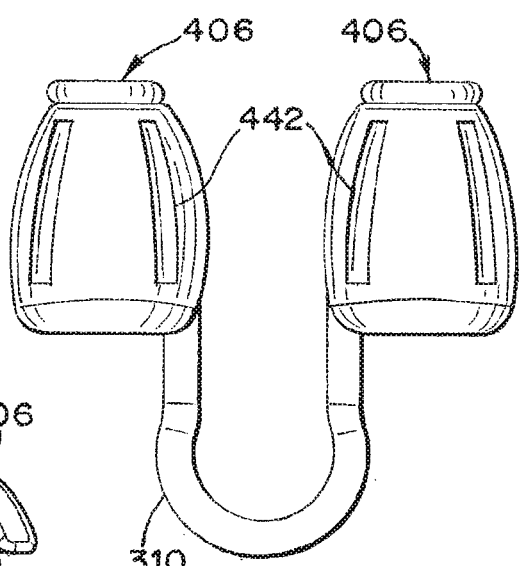
FIG. 56 is a top view of the nasal insert assembly shown in FIG. 55.
Figure 55:
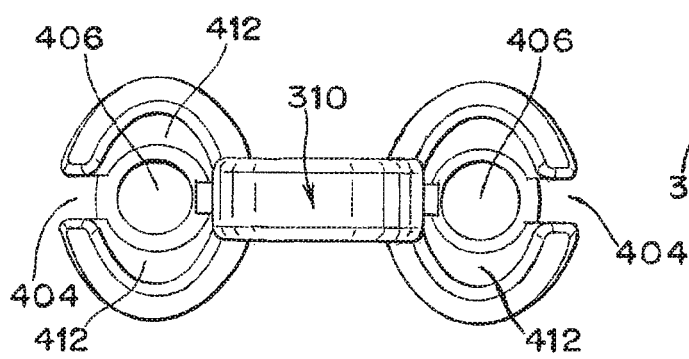
FIG. 55 is an end view of the nasal insert assembly shown in FIG. 54.

Referring to FIGS. 40-47 and 50-52, a nasal insert housing 400 is further configured with a grippable handle 402 hingedly attached to the housing at an end thereof opposite the hinged flap 406. In one embodiment, the handle has an opening 420 therethrough, such that the handle is shaped to receive a cannula tube or port/nipples as shown in FIG. 47. In this way, the insert does not interfere with the flow of oxygen at any time during use. Indeed, the resistance to exhaled gases will improve the oxygen saturation by not allowing the alveoli to collapse. The handle 402 is pivotally attached to the housing such that it may be gripped and pivoted outward away from the user to thereby extract the insert. The handle 402 may snap into either or both of the open and closed positions. Preferably, the insert is disposed entirely inside the nasal cavity, or vestibule, of the user during use, with the handle being moved to the closed position to avoid any protrusion of the insert outside of the vestibule. The handle, whether configured as a single insert embodiment or a bridge, may be magnetized, or made of metal, or include a metal insert 413 as shown in FIG. 52, that will be attracted by a magnet, such that a magnet or metal tool may be used to insert and extract the device. In addition, or alternatively, the handles may be configured with a filter material across the opening 420, such that the handles act as filters when closed. The handles may also be configured as a humidity moisture exchanger or medication holder.

Referring to the embodiments of FIGS. 40-52, whether configured as a pair of inserts connected with a bridge 310 or as separate units configured with a handle 402, a plurality of longitudinally extending recesses 442, or leak passageways, are defined on the exterior surface of the housing 400 and provide for some leakage of gas flow as well as provide for better retention of the housing as corresponding ribs grip the interior nasal tissue, with the tissue deforming into the recesses. The recesses may have a width of between about 0.1 and 1.6 mm, and in one embodiment between about 0.6 mm and 1.6 mm. The various devices may create a constant back pressure during exhalation in the range of about 5 to 20 cm of water, while the resistance is less than about 2 cm of water during inhalation.

In various embodiments, especially where configured as a single insert without a bridge providing stability, one or more interior, annular ribs 432, shown as three in one embodiment (FIGS. 41 and 43) or as one in another embodiment (FIGS. 51-52), may be spaced along the longitudinal axis 411 and lie in planes substantially perpendicular thereto. The ribs help maintain the overall shape of the insert and bias the insert against the nasal tissue. In one embodiment, undercuts defining the ribs are about 1.2 mm wide with a maximum depth of about 0.5 mm. The nasal insert includes a gap 404 and an interior passageway 412, with the user squeezing the insert to vary the gap 404 as the insert is inserted and/or extracted. Again, a leak or bleed opening 408 may be formed between the valve flap 406 and the gap 404 as shown in FIGS. 46 and 49.

The use of separate inserts may be particularly advantageous for users that, due to anatomical structure or nasal injury, use only one nostril for inhalation/exhalation. In addition, some users may have different internal heights in the vestibule area, thereby allowing the user to customize the individual insert to be used in each nasal cavity.

Referring to FIGS. 66-69, a nasal insert assembly 600 includes a pair of nasal inserts 602. In one embodiment, the inserts are spaced about 18 mm center to center, and have a length of about 11 mm. Each nasal insert has a user interface formed in a molded cup shape having a plurality of (shown as four) tongue-shaped petals or flaps 604 defining a curved, or conoid shaped insert portion. Although shown as four flaps, it should be understood that a greater or lesser number may also be suitable. It should be understood that the term conoid includes and refers to an outer surface portion of a sphere, cone, various spheroids, catenoids and/or paraboloids, and includes various convexly curved surfaces. The flaps 604 are separated by slits 606 formed in the insert, with one more end portions of the flaps moveable to form and opening in response to an inhalation flow, and then with the end portions closing against each other during exhalation or when at rest. The ends of the flaps may be trimmed in one embodiment, for example with a concavely curved recess, so to form a small opening 608 in the end of each insert. In one embodiment the opening 608 has a radius of about 1 mm. Alternatively, the opening may be omitted. An annular wall 610 is formed below the slits. In one embodiment, the annular wall 610 has a height of about 12 mm, and a width of about 11 mm. A spiral rib 612 is formed on the outer surface of the annular wall 610. As shown, a pair of inserts are connected with a bridge 310 made, for example, of silicone or a flexible like material, such that the assembly may be molded as a one piece molded unit. There are no additional pieces, such as an internal valve, required to make this nasal insert function.

Each insert 602 has an inlet port opening into an interior space. One or more of the flaps 604 will open to allow inhaled air to flow from the interior space to the patient's lungs. There is very little resistance, e.g., less than 2 cm of water, during inhalation. Upon exhalation, the flaps 604 are closed such that the exhaled air is directed along the outer surface of the flaps. The air travels down a circular, spiral flow path 616 defined by and between the spiral rib 612 and the nasal vestibule tissue engaged therewith, which creates a tortuous flow path for the exhaled air. The tortuous flow path produces a resistance to exhaled air flow which in turn creates an increased air pressure in the patient's respiratory system. The increase in pressure will be in the range between 5 and 20 cm of water. The spiral rib 612 may also be easily compressed such that the nasal tissue is partially allowed to settle in between the spiral rib and help maintain the nasal insert in the nasal cavity.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A nasal insert comprising:
   a housing comprising a circumferential wall defining an interior passage, wherein said wall comprises a longitudinal gap extending along a length thereof, wherein an outer peripheral dimension of said housing is adjustable by varying said gap; and
   a valve in communication with said interior passage, said valve limiting a fluid flow through said interior passage in at least one direction wherein said wall comprises an exterior surface defining a leak passageway, wherein said leak passageway comprises a longitudinally extending recess parallel to said gap.

2. The nasal insert of claim 1 wherein said valve comprises a hinged flap covering one end of said interior passage.

3. The nasal insert of claim 2 further comprising a grippable handle coupled to said housing opposite said hinged flap.

4. The nasal insert of claim 3 wherein said handle comprises an opening therethrough shaped to receive a cannula port.

5. The nasal insert of claim 4 wherein said handle is pivotally attached to said housing.

6. The nasal insert of claim 1 comprising a pair of said housings coupled respectively to a pair of said valves, with a bridge connecting said pair of housings.

7. The nasal insert of claim 1 wherein said housing comprises at least one rib formed around at least a portion of said interior passage.

8. The nasal insert of claim 7 wherein said at least one rib comprises an annular rib.

9. The nasal insert of claim 1 wherein said housing comprises a substantially spherical outer surface.

10. The nasal insert of claim 1 wherein said housing comprises a substantially cylindrical outer surface.

11. The nasal insert of claim 1 wherein said gap has a width of between about 2 mm and 4 mm.

12. The nasal insert of claim 1 wherein said gap is singular.

13. A method of providing resistance during exhalation comprising:
   providing a housing comprising a circumferential wall defining an interior passage defining a longitudinal flow path, wherein said wall comprises a longitudinal gap extending along a length thereof;
   squeezing said housing and thereby closing at least a portion of said gap;
   inserting said housing into a nasal passage of a user while said housing is being squeezed;
   releasing said housing and thereby letting said gap increase as said housing expands into said nasal passage of the user;
   inhaling through said housing and passing air through a valve in communication with said interior passage; and
   exhaling through said housing and limiting a flow of exhaled air through said interior passage with said valve and passing at least a portion of said exhaled air through said gap permitting a leakage a gas flow through a leak passageway defined between an exterior surface of said wall and said user's nasal tissue during said exhaling.

14. The method of claim 13 wherein said valve comprises a hinged flap covering one end of said interior passage, wherein said passing air through said valve comprise opening said flap.

15. The method of claim 13 wherein said leak passageway comprises a longitudinally extending recess formed in said exterior surface parallel to said gap.

16. The method of claim 13 further comprising creating a constant back pressure during exhalation in a range of about 5 to 20 cm $H_2O$.

17. The method of claim 13 wherein said gap is singular.

* * * * *